United States Patent [19]

Fuchs et al.

[11] Patent Number: 5,391,560
[45] Date of Patent: Feb. 21, 1995

[54] SUBSTITUTED CARBAMOYLPYRAZOLINES

[75] Inventors: Rainer Fuchs, Wuppertal; Johannes Kanellakopulos, Hilden; Christoph Erdelen, Leichlingen; Wilhelm Stendel, Wuppertal, all of Germany

[73] Assignee: Bayer Aktiengesellschaft, Leverkusen, Germany

[21] Appl. No.: 129,929

[22] Filed: Sep. 30, 1993

[30] Foreign Application Priority Data

Oct. 7, 1992 [DE] Germany .............................. 4233715

[51] Int. Cl.$^6$ ..................... C02D 403/04; A01N 47/38
[52] U.S. Cl. ................................ 514/363; 514/364; 514/384; 514/386; 514/404; 548/137; 548/144; 548/263.2; 548/312.4; 548/365.4
[58] Field of Search ............ 548/263.2, 144, 137, 548/365.4, 312.4; 514/363, 364, 384, 386, 401

[56] References Cited

U.S. PATENT DOCUMENTS 5,086,183  2/1992  Fuchs ................................ 548/110

FOREIGN PATENT DOCUMENTS 334133  9/1989  European Pat. Off. .
0466408  1/1991  European Pat. Off. .
0529452  3/1993  European Pat. Off. .

*Primary Examiner*—Robert Gerstl
*Attorney, Agent, or Firm*—Sprung, Horn, Kramer & Woods

[57] ABSTRACT

The invention relates to new substituted carbamoylpyrazolines

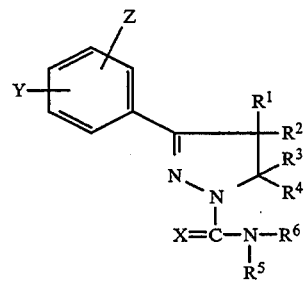

to processes in their preparation, and to their use as pesticides.

5 Claims, No Drawings

SUBSTITUTED CARBAMOYLPYRAZOLINES

The invention relates to new substituted carbamoylpyrazolines, to processes for their preparation, and to their use as pesticides.

It has been disclosed that certain pyrazoline derivatives have a good activity against animal pests.

See, in this context, for example DE-A 2,700,258, U.S. Pat. No. 4,174,393, DE-A 2,529,689, U.S. Pat. No. 4,070,365 and EP-A 0,466,408.

However, the level, or duration, of action of these previously known compounds is not satisfactory in all fields of application, in particular in connection with certain organisms or when low concentrations are applied.

New substituted carbamoylpyrazolines of the general formula (I)

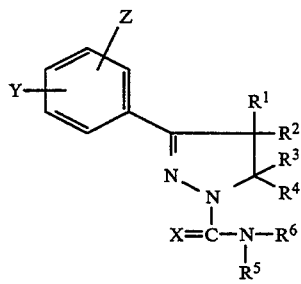

in which $R^1$ represents an azolinone, azolinethione or azolineimino radical, each of which is optionally substituted and bonded via nitrogen, $R^2$ represents hydrogen, alkyl, optionally substituted cycloalkyl, halogenoalkyl, halogenoalkylthio or alkoxycarbonyl, $R^3$ represents hydrogen, alkyl or a group

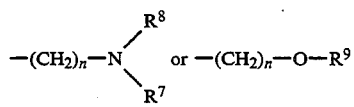

in which $R^7$ and $R^8$ in each case independently of one another represent hydrogen, alkyl or aryl and $R^9$ represents hydrogen, alkyl or aryl and n represents the numbers 1 to 6, $R^4$ represents hydrogen or alkyl, $R^5$ represents hydrogen, alkyl, phenyl or alkylthio, $R^6$ represents optionally substituted alkyl, optionally substituted cycloalkyl or the radical

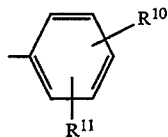

in which $R^{10}$ and $R^{11}$ can be identical or different and represent hydrogen, halogen, alkyl, nitro, cyano, halogenoalkyl, alkoxy, halogenoalkoxy, alkylthio, halogenoalkylthio, optionally substituted phenoxy, optionally substituted mono- or dialkylamino, optionally substituted cycloalkyl, alkoxycarbonyl, optionally substituted arylthio, alkenyloxy, alkinyl, alkylthionyl, alkylsulphonyl, halogenoalkylthionyl, halogenoalkylsulphonyl, halogenoalkoxycarbonyl, or in which $R^{10}$ and $R^{11}$ together represent a bivalent radical which optionally contains one or two oxygen atoms and which is optionally substituted, X represents oxygen or sulphur and Y and Z can be identical or different and represent hydrogen, alkyl, halogen, halogenoalkyl, alkoxy, alkylthio, halogenoalkoxy, halogenoalkylthio, alkoxycarbonyl, halogenoalkoxycarbonyl, optionally substituted aryloxy, optionally substituted arylthio, alkenyloxy, alkinyl, alkylthionyl, alkylsulphonyl, halogenoalkylthionyl, halogenoalkylsulphonyl, nitro, or cyano, or in which Y and Z together represent 3,4-methylenedioxy or 3,4-ethylenedioxy, each of which is optionally substituted by halogen, have now been found.

Furthermore, it has been found that the new substituted carbamoylpyrazolines of the general formula (I)

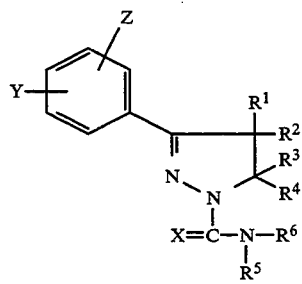

in which $R^1$ represents an azolinone, azolinethione or azolineimino radical, each of which is optionally substituted, $R^2$ represents hydrogen, alkyl, optionally substituted cycloalkyl, halogenoalkyl, halogenoalkylthio or alkoxycarbonyl, $R^3$ represents hydrogen, alkyl or a group

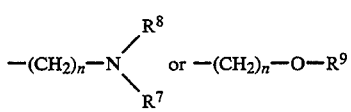

in which $R^7$ and $R^8$ in each case independently of one another represent hydrogen, alkyl or aryl and $R^9$ represents hydrogen, alkyl or aryl and n represents the numbers 1 to 6, $R^4$ represents hydrogen or alkyl, $R^5$ represents hydrogen, alkyl, phenyl or alkylthio, $R^6$ represents optionally substituted alkyl, optionally substituted cycloalkyl or the radical

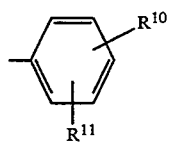

in which $R^{10}$ and $R^{11}$ can be identical or different and represent hydrogen, halogen, alkyl, nitro, cyano, halogenoalkyl, alkoxy, halogenoalkoxy, alkylthio, halogenoalkylthio, optionally substituted phenoxy, optionally substituted mono- or dialkylamino, optionally substituted cycloalkyl, alkoxycarbonyl, optionally substituted arylthio, alkenyloxy, alkinyl, alkylthionyl, alkylsulphonyl, halogenoalkylthionyl, halogenoalkylsulphonyl, halogenoalkoxycarbonyl, or in which $R^{10}$ and $R^{11}$ together represent a bivalent radical which optionally contains one or two oxygen atoms and which is optionally substituted, X represents oxygen or sulphur and Y and Z can be identical or different and represent hydrogen, alkyl, halogen, halogenoalkyl, alkoxy, alkylthio, halogenoalkoxy, halogenoalkylthio, alkoxycarbonyl, halogenoalkoxycarbonyl, optionally substituted aryloxy, optionally substituted arylthio, alkenyloxy, alkinyl, alkylthionyl, alkylsulphonyl, halogenoalkylthionyl, halogenoalkylsulphonyl, nitro, or cyano, or in which Y and Z together represent 3,4-methylenedioxy or 3,4-ethylenedioxy, each of which is optionally substituted by halogen, are obtained when A) to obtain carbamoylpyrazolines of the formula (I) in which $R^5$ represents hydrogen, pyrazoline derivatives of the formula (II)

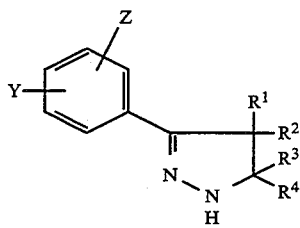

(II)

in which Y, Z, $R^1$, $R^2$, $R^2$, $R^3$ and $R^4$ have the abovementioned meaning are reacted with isocyanates or isothiocyanates of the formula (III)

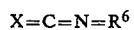

$X=C=N=R^6$ (III)

in which X and R6 have the abovementioned meaning, if appropriate in the presence of bases, or when B) to obtain carbamoylpyrazolines of the formula (I) in which R2 represents alkyl, cycloalkyl, halogenoalkyl, halogenoalkylthio or alkoxycarbonyl, compounds of the formula (IV)

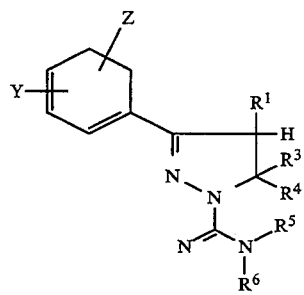

(IV)

in which X, Y, Z, $R^1$, $R^3$, $R^4$, $R^5$ and $R^6$ have the abovementioned meaning, are reacted with compounds of the formula (V)

Hal-$R^{2-1}$ (V)

in which

Hal represents halogen and $R^{2-1}$ represents alkyl, optionally substituted cycloalkyl, halogenoalkyl, halogenoalkylthio or alkoxycarbonyl, in an anhydrous medium and with addition of a strong base.

Finally, it has been found that the new carbamoylpyrazolines of the general formula (I) have a very good activity against pests and, in particular, are very good insecticidal and acaricidal activity.

Surprisingly, the substituted carbamoylpyrazolines according to the invention display a considerably better insecticidal activity against insects and arachnids which are phytopathogenic and which parasitise warm-blooded species than compounds which are similar chemically and from the point of view of their action and which are known from the prior art.

Formula (I) provides a general definition of the substituted carbamoylpyrazolines according to the invention. Preferred compounds of the formula (I) are those in which $R^1$ represents an azolinone, azolinethione or azolineimino radical, optionally monosubstituted or disubstituted by identical or different substituents and bonded via nitrogen, from the series comprising

(R1-a)

(R1-b)

(R1-c)

(R1-d)

(R1-e)

(R1-f)

(R1-g)

(R1-h)

(R1-i)

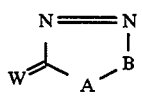 (R¹-k)

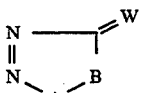 (R¹-l)

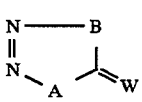 (R¹-m)

in which
one of the groups A or B represents nitrogen and in each case the other one (B or A) represents oxygen, sulphur or the group —N alkyl($C_1$-$C_4$) or a methylene group —$CH_2$—, W represents oxygen, sulphur or the group —N alkyl($C_1$-$C_6$), the following substituents being suitable: alkyl ($C_1$-$C_6$), alkoxy($C_1$-$C_6$), alkyl($C_1$-$C_6$)thio, amino, alkyl ($C_1$-$C_6$)amino, halogenoalkyl ($C_1$-$C_4$), dialkyl ($C_1$-$C_6$) amino, and phenyl which is optionally substituted by halogen, alkyl($C_1$-$C_4$), alkoxy($C_1$-$C_4$), halogenoalkyl(-$C_1$-$C_4$), halogenoalkoxy($C_1$-$C_4$)- or halogenoalkyl ($C_1$-$C_4$)thio, $R^2$ represents hydrogen, alkyl ($C_1$-$C_6$), or represents cycloalkyl($C_3$-$C_7$) which is optionally substituted by halogen or halogenoalkyl-($C_1$-$C_4$); or represents halogenoalkyl ($C_1$-$C_4$), halogenoalkyl ($C_1$-$C_4$) thio or alkoxy($C_1$-$C_6$)carbonyl, $R^3$ represents hydrogen, alkyl($C_1$-$C_6$) or a group

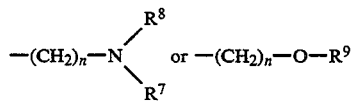

in which
$R^7$ and $R^8$ in each case independently of one another represent hydrogen, alkyl ($C_1$-$C_6$), or phenyl which is optionally substituted by alkyl ($C_1$-$C_4$), alkoxy($C_1$-$C_4$), alkyl($C_1$-$C_4$)thio, halogen, halogenoalkyl($C_1$-$C_4$), halogenoalkoxy($C_1$-$C_4$) or halogenoalkyl($C_1$-$C_4$) thio and $R^9$ represents hydrogen, alkyl($C_1$-$C_6$) or optionally substituted phenyl, suitable substituents being the phenyl substituents mentioned in the case of $R^8$, and n represents the numbers 1 to 4, $R^4$ represents hydrogen or alkyl ($C_1$-$C_6$), $R^5$ represents hydrogen, alkyl($C_1$-$C_6$), phenyl or alkyl(-$C_1$-$C_6$)thio, $R^6$ represents alkyl ($C_1$-$C_6$) which is optionally substituted by halogen, halogenoalkyl($C_1$-$C_4$) or halogenoalkoxy($C_1$-$C_4$), or represents cycloalkyl($C_3$-$C_7$) which is optionally substituted by halogen, halogenoalkyl($C_-C_4$) or halogenoalkoxy($C_1$-$C_4$), or represents the radical

in which
$R^{10}$ and $R^{11}$ can be identical or different and represent halogen, alkyl($C_1$-$C_6$), nitro, cyano, halogenoalkyl($C_1$-$C_4$), alkoxy($C_1$-$C_6$), halogenoalkoxy($C_1$-$C_4$), alkyl($C_1$-$C_4$)thio, halogenoalkyl(-$C_1$-$C_4$)thio, or represent phenoxy or phenylthio, each of which is optionally substituted by halogen, halogenoalkyl ($C_1$-$C_4$) or alkoxy($C_1$-$C_4$), or represents mono- or dialkylamino, each of which has 1 to 6 carbon atoms in the alkyl radical and each of which is optionally substituted by halogen, alkoxy($C_1$-$C_4$) or halogenoalkyl($C_1$-$C_4$ ), or represent cycloalkyl ($C_1$-$C_7$) which is optionally substituted by alkyl ($C_1$-$C_4$), alkoxy($C_1$-$C_4$), halogen or alkyl ($C_1$-$C_4$)thio, or represent alkoxy($C_1$-$C_4$) carbonyl, alkenyl($C_2$-$C_6$)oxy, alkinyl($C_2$-$C_6$), alkyl ($C_1$-$C_4$)thionyl, alkyl ($C_1$-$C_4$)sulphonyl, halogenoalkyl ($C_1$-$C_4$)thionyl, halogenoalkyl ($C_1$-$C_4$)sulphonyl or halogenoalkoxy($C_1$-$C_4$)carbonyl, or in which $R^{10}$ and $R^{11}$ together represent one of the following bivalent radicals

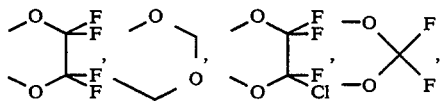

X represents oxygen or sulphur and
Y and Z can be identical or different and represent hydrogen, alkyl($C_1$-$C_6$), halogen, halogenoalkyl(-$C_1$-$C_6$), alkoxy($C_1$-$C_6$), alkyl($C_1$-$C_6$)thio, halogenoalkoxy($C_1$-$C_4$), halogenoalkyl($C_1$-$C_4$)thio, alkoxy ($C_1$-$C_4$) carbonyl, halogenoalkoxy($C_1$-$C_4$ ) carbonyl, or represent phenoxy or phenylthio, each of which is optionally substituted by halogen, alkyl($C_1$-$C_4$), alkoxy($C_1$-$C_4$) or halogenoalkyl(-$C_2$-$C_4$), or represent alkenyl ($C_2$-$C_6$)oxy, alkinyl ($C_2$-$C_6$ ), alkyl($C_1$-$C_4$)thionyl, alkyl ($C_1$-$C_4$)sulphonyl, halogenoalkyl ($C_1$-$C_4$)thionyl, halogenoalkyl ($C_1$-$C_4$) sulphonyl, nitro or cyano, or in which
Y and Z together represent 3,4-methylenedioxy or 3,4-ethylenedioxy, each of which is optionally substituted by fluorine and/or chlorine.

Particularly preferred compounds of the formula (I) are those in which
$R^1$ represents an azolinone, azolinethione or azolineimino radical, optionally monosubstituted or disubstituted by identical or different substituents and bonded via nitrogen, from the series comprising

 (R¹-a)

 (R¹-b)

-continued

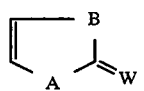 (R¹-c)

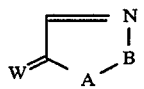 (R¹-d)

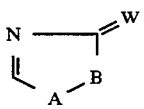 (R¹-e)

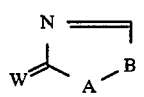 (R¹-f)

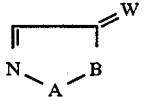 (R¹-g)

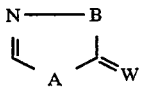 (R¹-h)

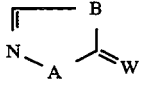 (R¹-i)

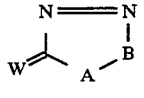 (R¹-k)

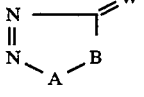 (R¹-l)

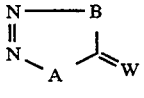 (R¹-m)

in which
one of the groups A or B represents nitrogen and in each case the other one (B or A) represents oxygen, sulphur or the group —N alkyl($C_1$-$C_4$) or a methylene group —$CH_2$—, W represents oxygen, sulphur or the group —N alkyl($C_1$-$C_4$)

and the following substituents being suitable: alkyl($C_1$-$C_4$), alkoxy($C_1$-$C_4$), alkyl($C_1$-$C_4$)thio, amino, alkyl($C_1$-$C_4$)amino, halogenoalkyl($C_1$-$C_4$), dialkyl($C_1$-$C_4$) amino and phenyl which is optionally substituted by fluorine, chlorine, bromine, methyl, ethyl, methoxy, ethoxy, halogenoalkyl($C_1$-$C_2$), halogenoalkoxy($C_1$-$C_2$) or halogenoalkyl ($C_1$-$C_2$)thio, $R^2$ represents hydrogen, alkyl ($C_1$-$C_4$), or cycloalkyl ($C_3$-$C_6$) which is optionally substituted by fluorine, chlorine, bromine or halogenoalkyl($C_1$-$C_3$); or represents halogenoalkyl ($C_1$-$C_3$), halogenoalkyl($C_1$-$C_3$)thio or alkoxy($C_1$-$C_4$)carbonyl, $R^3$ represents hydrogen, alkyl ($C_1$-$C_4$) or a group

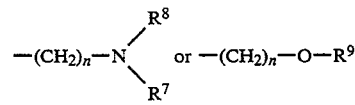

in which
$R^7$ and $R^8$ in each case independently of one another represent hydrogen, alkyl($C_1$-$C_4$), or phenyl which is optionally substituted by methyl, ethyl, methoxy, ethoxy, methylthio, ethylthio, fluorine, chlorine, bromine, halogenoalkyl($C_1$-$C_2$), halogenoalkoxy($C_1$-$C_2$) or halogenoalkyl($C_1$-$C_2$)thio and $R^9$ represents hydrogen, alkyl($C_1$-$C_4$), or phenyl, which is optionally monosubstituted or polysubstituted by identical or different substituents, suitable substituents being the phenyl substituents mentioned in the case of $R^8$, and n represents the numbers 1, 2 or 3, $R^4$ represents hydrogen or alkyl ($C_1$-$C_4$), $R^5$ represents hydrogen, alkyl($C_1$-$C_4$), phenyl or alkyl($C_1$-$C_3$)thio, $R^6$ represents alkyl ($C_1$-$C_4$) which is optionally substituted by fluorine, chlorine, bromine, halogenoalkyl($C_1$-$C_3$) or halogenoalkoxy ($C_1$-$C_3$), or represents cycloalkyl($C_1$-$C_6$) which is optionally substituted by fluorine, chlorine, bromine, halogenoalkyl($C_1$-$C_3$) or halogenoalkoxy($C_1$-$C_3$), or represents the radical

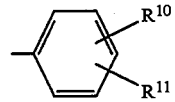

in which
$R^{10}$ and $R^{11}$ can be identical or different and represent fluorine, chlorine, bromine, iodine, alkyl ($C_1$-$C_4$), nitro, cyano, halogenoalkyl ($C_1$-$C_3$), alkoxy ($C_1$-$C_4$), halogenoalkoxy ($C_1$-$C_3$), alkyl($C_1$-$C_3$)thio or halogenoalkyl($C_1$-$C_3$)thio, or represent phenoxy which is optionally substituted by fluorine, chlorine, bromine, halogenoalkyl($C_1$-$C_3$) or alkoxy ($C_1$-$C_4$), or represent mono- or dialkylamino, each of which has 1 to 4 carbon atoms in the alkyl radical and each of which is optionally substituted by fluorine, chlorine, bromine, alkoxy ($C_1$-$C_3$) or halogenoalkyl ($C_1$-$C_3$), or represent cycloalkyl($C_3$-$C_6$) which is optionally substituted by alkyl($C_1$-$C_3$), alkoxy($C_1$-$C_3$), fluorine, chlorine, bromine or alkyl($C_1$-$C_3$)thio, or in which $R^{10}$ and $R^{11}$ together represent one of the following bivalent radicals

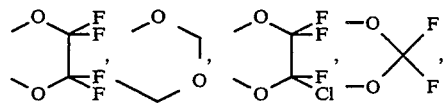

X represents oxygen or sulphur and

Y and Z can be identical or different and represent hydrogen, alkyl ($C_1$-$C_4$), fluorine, chlorine, bromine, halogenoalkyl ($C_1$-$C_4$), alkoxy($C_1$-$C_4$), alkyl ($C_1$-$C_4$)thio, halogenoalkoxy($C_1$-$C_3$), halogenoalkyl($C_1$-$C_3$)thio, alkoxy($C_1$-$C_3$) carbonyl, or phenoxy or phenylthio, each of which is optionally substituted by fluorine, chlorine, bromine, alkyl(-

$C_1$–$C_3$), alkoxy($C_1$–$C_3$) or halogenoalkyl ($C_1$–$C_3$), or represent alkenyl ($C_2$–$C_4$)oxy, alkinyl($C_2$–$C_4$), alkyl($C_1$–$C_3$)thionyl, alkyl($C_1$–$C_4$)sulphonyl halogenoalkyl ($C_1$–$C_3$)thionyl, halogenoalkyl ($C_1$–$C_3$)sulphonyl, nitro or cyano, or in which Y and Z together represent 3,4-methylenedioxy or 3,4-ethylenedioxy, each of which is optionally substituted by fluorine and/or chlorine.

Especially preferred compounds of the formula (I) are those in which $R^1$ represents an azolinone, azolinethione or azolineimino radical, in each case optionally monosubstituted or disubstituted by identical or different substituents and bonded via nitrogen, from the series comprising

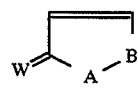
($R^1$-b)

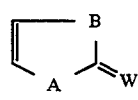
($R^1$-c)

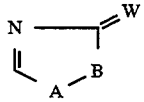
($R^1$-e)

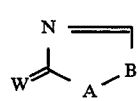
($R^1$-f)

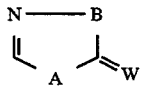
($R^1$-h)

or

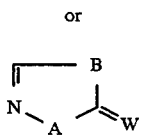
($R^1$-i)

in which one of the groups A or B represents nitrogen and the other one (B or A) represents oxygen, sulphur or the group —$NCH_3$ or a methylene group —$CH_2$—, W represents oxygen or sulphur, and the following substituents being suitable: methyl, ethyl, n-propyl, i-propyl, t-butyl, methoxy, methylthio, trifluoromethyl, chlorodifluoromethyl, fluorodichloromethyl, and phenyl which is optionally substituted by fluorine, chlorine, bromine, methyl, methoxy, trifluoromethyl or trifluoromethoxy $R^2$ represents hydrogen, methyl, ethyl, n-propyl, i-propyl or alkoxy($C_1$–$C_2$)carbonyl, $R^3$ represents hydrogen, methyl, ethyl, n-propyl, i-propyl or the group

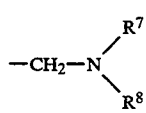

in which $R^7$ and $R^8$ in each case independently of one another represent hydrogen, methyl, ethyl, n-propyl or i-propyl, $R^4$ represents hydrogen, methyl, ethyl or n-propyl, $R^5$ represents hydrogen, methyl, ethyl, n-propyl, i-propyl, phenyl or alkyl($C_1$–$C_2$)thio, $R^6$ represents methyl, ethyl, n-propyl or i-propyl, each of which is optionally substituted by fluorine, chlorine, halogenoalkyl($C_1$–$C_3$) or halogenoalkoxy($C_1$–$C_3$), or represents cycloalkyl($C_3$–$C_6$) which is optionally substituted by fluorine, chlorine, halogenoalkyl($C_1$–$C_3$) or halogenoalkoxy($C_1$–$C_3$), or represents the radical

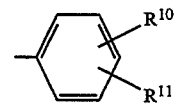

in which $R^{10}$ and $R^{11}$ can be identical or different and represent fluorine, chlorine, bromine, iodine, methyl, ethyl, n-propyl, i-propyl, tert.-butyl, nitro, cyano, halogenoalkyl($C_1$–$C_3$), alkoxy($C_1$–$C_3$), halogenoalkoxy($C_1$–$C_3$), alkyl ($C_1$–$C_3$)thio, halogenoalkyl($C_1$–$C_3$)thio, or represent phenoxy which is optionally substituted by fluorine, chlorine, halogenoalkyl($C_1$–$C_3$), methoxy, ethoxy, methyl or ethyl, or represent mono- or dialkylamino, each of which has 1 to 3 carbon atoms in the alkyl radical and each of which is optionally substituted by fluorine, chlorine, methoxy, ethoxy or halogenoalkyl ($C_1$–$C_3$ ), or represent cycloalkyl($C_3$–$C_6$) which is optionally substituted by methyl, ethyl, methoxy, ethoxy, fluorine, chlorine or alkyl ($C_1$–$C_3$) thio, or in which $R^{10}$ and $R^{11}$ together represent one of the following bivalent radicals

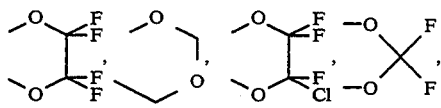

X represents oxygen or sulphur and

Y and Z can be identical or different and represent hydrogen, methyl, ethyl, n-propyl, i-propyl, fluorine, chlorine, halogenoalkyl ($C_1$–$C_3$), methoxy, ethoxy, n-propyloxy, i-propyloxy, alkyl ($C_1$–$C_3$)thio, halogenoalkoxy ($C_1$–$C_3$), halogenoalkyl ($C_1$–$C_3$)thio, alkoxy ($C_1$–$C_3$)carbonyl, or represent phenoxy or phenylthio, each of which is optionally substituted by fluorine, chlorine, methyl, ethyl, methoxy, ethoxy or halogenoalkyl ($C_1$–$C_3$), or represent alkenyl ($C_3$–$C_4$)oxy, alkinyl($C_2$–$C_4$), alkyl($C_1$–$C_3$)thionyl, alkyl ($C_1$–$C_3$)sulphonyl, halogenoalkyl ($C_1$–$C_3$)thionyl, halogenoalkyl ($C_1$–$C_3$)sulphonyl, nitro or cyano, or in which Y and Z together represent 3,4-methylenedioxy or 3,4-ethylenedioxy, each of which is optionally substituted by fluorine and/or chlorine.

The meaning of the substituent halogenoalkyl in the radicals halogenoalkyl, halogenoalkoxy, halogenoalkylthio, halogenoalkylthionyl and halogenoalkylsulphonyl contains preferably 1 to 4, in particular 1 or 2, carbon atoms and preferably 1 to 5, in particular 1 to 3, identical or different halogen atoms, suitable halogen atoms preferably being fluorine, chlorine and bromine, in particular fluorine and chlorine. Examples which may be mentioned are trifluoromethyl, chlorodifluoromethyl, bromomethyl, 2,2,2-trifluoroethyl and pentafluoroethyl.

The following substituted carbamoylpyrazolines which have the following formulae and which are listed in Tables 1A to 1I and 1K to 1M may be mentioned individually in addition to the compounds mentioned in the preparation examples:

TABLE 1A

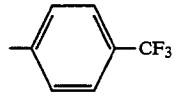

| Y | Z | X | $R^2$ | $R^3$ | $R^4$ | $R^5$ | $R^6$ |
|---|---|---|---|---|---|---|---|
| H | H | O | H | H | H | H | ―⟨⟩―$CF_3$ |
| H | H | O | H | H | H | H | ―⟨⟩―$OCF_3$ |
| 4-$CF_3$ | H | O | H | H | H | H | ―⟨⟩―$CF_3$ |
| 4-$CF_3$ | H | O | H | H | H | H | ―⟨⟩―Cl |
| 4-$CF_3$ | H | O | H | H | H | H | ―⟨⟩―$OCF_3$ |
| 4-Br | H | O | H | H | H | H | ―⟨⟩―$CF_3$ |
| 3-$CF_3$ | H | O | H | H | H | H | ―⟨⟩―Cl |
| 3-$CF_3$ | H | O | H | H | H | H | ―⟨⟩―$OCHF_2$ |
| 4-F | H | O | H | H | H | H | ―⟨⟩―Cl |
| 4-F | H | O | H | H | H | H | ―⟨⟩―$CF_3$ |

TABLE 1A-continued

| Y | Z | X | R² | R³ | R⁴ | R⁵ | R⁶ |
|---|---|---|----|----|----|----|-----|
| 4-F | H | O | H | H | H | H | —C₆H₄—OCF₃ (4-) |
| 4-F | H | O | H | H | H | H | —C₆H₄—OCHF₂ (4-) |
| 4-F | H | O | H | H | H | H | —C₆H₄—SCF₃ (4-) |
| 4-F | H | O | H | H | H | H | —C₆H₄—OCF₂—CHF₂ (4-) |
| 4-F | H | O | H | H | H | H | —C₆H₄—CHF₂ (4-) |
| 4-F | H | O | H | H | H | H | —C₆H₄—F (4-) |
| 4-Cl | H | O | H | H | H | H | —C₆H₄—CF₃ (4-) |
| 4-OCHF₂ | H | O | H | H | H | H | —C₆H₄—OCF₃ (4-) |
| 4-F | H | O | H | H | H | H | —C₆H₁₀—CF₃ (4-, cyclohexyl) |
| 4-F | H | O | H | H | H | H | —C₆H₄—OCF₂Cl (4-) |
| 4-F | H | O | CH₃ | H | H | H | —C₆H₄—OCF₃ (4-) |

TABLE 1A-continued

[Structure: phenyl ring with Y and Z substituents, connected to a pyrazoline system with R2, R3, R4 substituents, N-N with C(=X)-N(R5)(R6) group, and a pyrazolone-methyl-N-methyl carbonyl group]

| Y | Z | X | R² | R³ | R⁴ | R⁵ | R⁶ | (aryl group) |
|---|---|---|----|----|----|----|----|--------------|
| 4-F | H | O | —COOCH₃ | H | H | H | | 4-SCF₃-phenyl |
| 4-F | H | S | H | H | H | H | | 4-OCHF₂-phenyl |
| 4-Cl | H | O | H | H | H | H | | 3-F-4-CF₃-phenyl |
| 4-Cl | H | O | H | H | H | H | | 4-OCF₃-phenyl |
| 4-Cl | H | O | H | H | H | H | | 4-OCHF₂-phenyl |
| 4-Cl | H | O | H | H | H | H | | 3,4-(OCF₂CF₂O)-phenyl |
| 4-OCHF₂ | H | O | H | H | H | H | | 4-CF₃-phenyl |
| 4-OCHF₂ | H | O | H | H | H | H | | 4-OCF₃-phenyl |
| 4-OCHF₂ | H | O | H | H | H | H | | 4-Cl-phenyl |
| 4-OCHF₂ | H | O | H | H | H | H | | 4-OCF₂CHF₂-phenyl |

TABLE 1A-continued

[Structure: phenyl(Y,Z)-substituted pyrazoline with N-N-C(=X)-N(R5)(R6) and triazolinone ring bearing CH3 and N-CH3]

| Y | Z | X | R² | R³ | R⁴ | R⁵ | R⁶ |
|---|---|---|----|----|----|----|----|
| 4-OCH₂CF₃ | H | O | H | H | H | H | –C₆H₄–4-CF₃ |
| 4-OCH₂CF₃ | H | O | H | H | H | H | –C₆H₄–4-Cl |
| 4-CF₃ | H | O | H | H | H | H | –C₆H₁₀–4-CF₃ (cyclohexyl, H) |

TABLE 1B

[Structure: 4-phenyl-substituted pyrazoline with triazolinone bearing N-CH3, fused with phenyl(Y,Z), and X=C–N(R5)(R6)]

| Y | Z | X | R² | R³ | R⁴ | R⁵ | R⁶ |
|---|---|---|----|----|----|----|----|
| 4-CF₃ | H | O | H | H | H | H | –C₆H₄–4-OCF₃ |
| H | H | O | H | H | H | H | –C₆H₄–4-CF₃ |
| 4-t.-butyl | H | O | H | H | H | H | –C₆H₄–4-CF₃ |
| 3-CF₃ | H | O | H | H | H | H | –C₆H₄–4-OCF₃ |
| 4-CH₃ | H | O | H | H | H | H | –C₆H₄–4-CF₃ |
| 4-CH₃ | H | O | H | H | H | H | –C₆H₄–4-Cl |
| 4-Cl | H | O | H | H | H | H | –C₆H₄–4-CF₃ |
| 4-Cl | H | O | H | H | H | H | –C₆H₄–4-SCF₂Cl |

TABLE 1B-continued

Structure: pyrazoline with Y-phenyl, Z substituent, triazolinone bearing phenyl and N-CH3, with R2, R3, R4, and X=C-N(R5)-R6 substituents.

| Y | Z | X | R2 | R3 | R4 | R5 | R6 |
|---|---|---|----|----|----|----|----|
| 4-F | H | O | H | H | H | H | 4-OCF3-phenyl |
| 4-Cl | H | O | H | CH3 | H | H | 4-CF3-phenyl |
| 4-OCHF2 | H | O | H | CH3 | H | H | 4-OCF3-phenyl |
| 4-F | H | O | H | CH3 | CH3 | H | 4-CF3-phenyl |
| 4-CF3 | H | O | H | H | H | H | 3-F-4-CF3-phenyl |
| 4-Cl | H | O | H | H | H | H | 4-Cl-phenyl |
| 4-Br | H | O | H | H | H | H | 4-OCF3-phenyl |
| 4-Cl | H | O | H | H | H | H | 4-CF3-cyclohexyl |

TABLE 1C

Structure: pyrazoline with Y-phenyl, Z substituent, triazolinethione bearing CH3 and N-CH3, with R2, R3, R4, and X=C-N(R5)-R6 substituents.

| Y | Z | X | R2 | R3 | R4 | R5 | R6 |
|---|---|---|----|----|----|----|----|
| H | H | O | H | H | H | H | 4-CF3-phenyl |
| H | H | O | H | H | H | H | 4-OCF3-phenyl |
| 4-CF3 | H | O | H | H | H | H | 4-CF3-phenyl |

TABLE 1C-continued
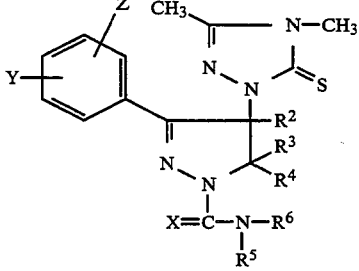
| Y | Z | X | R² | R³ | R⁴ | R⁵ | R⁶ |
|---|---|---|----|----|----|----|----|
| 4-CF₃ | H | O | H | H | H | H | 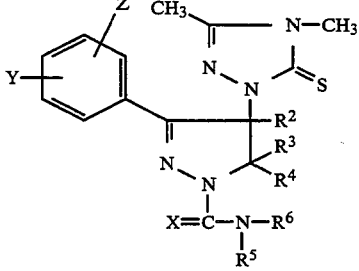 —⟨ ⟩—Cl |
| 4-CF₃ | H | O | H | H | H | H | —⟨ ⟩—OCF₃ |
| 4-Br | H | O | H | H | H | H | —⟨ ⟩—CF₃ |
| 3-CF₃ | H | O | H | H | H | H | —⟨ ⟩—Cl |
| 3-CF₃ | H | O | H | H | H | H | —⟨ ⟩—OCHF₂ |
| 4-Br | H | O | H | H | H | H | —⟨ ⟩—Cl |
| 4-F | H | O | H | H | H | H | —⟨ ⟩—Br |
| 4-F | H | O | H | H | H | H | —⟨ ⟩—OCF₃ |
| 4-F | H | O | H | H | H | H | —⟨ ⟩—OCHF₂ |
| 4-F | H | O | H | H | H | H | —⟨ ⟩—SCF₃ |
| 4-F | H | O | H | H | H | H | —⟨ ⟩—OCF₂—CHF₂ |

TABLE 1C-continued
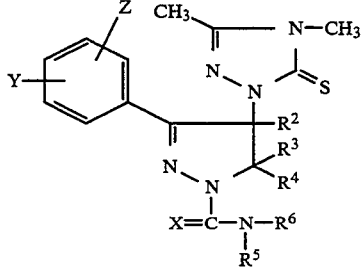
| Y | Z | X | R² | R³ | R⁴ | R⁵ | R⁶ | |
|---|---|---|----|----|----|----|----|---|
| 4-F | H | O | H | H | H | H | | 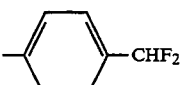 |
| 4-F | H | O | H | H | H | H | | 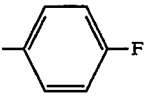 |
| 4-Cl | H | O | H | H | H | H | | 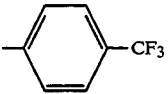 |
| 4-OCHF₂ | H | O | H | H | H | H | | 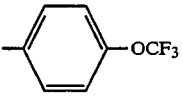 |
| 4-F | H | O | H | H | H | H | | 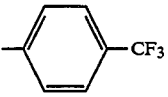 |
| 4-F | H | O | H | H | H | H | | 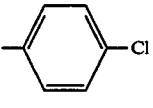 |
| 4-F | H | O | CH₃ | H | H | H | | 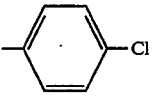 |
| 4-F | H | O | —COOCH₃ | H | H | | | 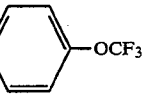 |
| 4-F | H | S | H | H | H | H | | 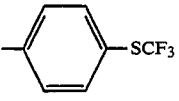 |
| 4-F | H | O | H | CH₃ | H | H | | 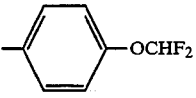 |
| 4-Cl | H | O | H | H | H | H | | 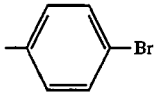 |

TABLE 1C-continued

| Y | Z | X | R² | R³ | R⁴ | R⁵ | R⁶ |
|---|---|---|---|---|---|---|---|
| 4-Cl | H | O | H | H | H | H | —C₆H₄—OCF₃ (4-OCF₃-phenyl) |
| 4-Cl | H | O | H | H | H | H | —C₆H₄—OCHF₂ (4-OCHF₂-phenyl) |
| 4-Cl | H | O | H | H | H | H | phenyl-O-CF₂-CF₂-O (benzodioxole-type, tetrafluoro) |
| 4-OCHF₂ | H | O | H | H | H | H | 4-CF₃-cyclohexyl |
| 4-OCHF₂ | H | O | H | H | H | H | 4-OCF₃-phenyl |

TABLE 1D

| Y | Z | X | R² | R³ | R⁴ | R⁵ | R⁶ |
|---|---|---|---|---|---|---|---|
| 4-OCHF₂ | H | O | H | H | H | H | 4-Cl-phenyl |

TABLE 1D-continued

| Y | Z | X | R² | R³ | R⁴ | R⁵ | R⁶ |
|---|---|---|----|----|----|----|----|
| 4-OCHF₂ | H | O | H | H | H | H | -C₆H₄-OCF₂-CHF₂ (4-) |
| 4-OCH₂CF₃ | H | O | H | H | H | H | -C₆H₄-CF₃ (4-) |
| 4-OCH₂CF₃ | H | O | H | H | H | H | -C₆H₄-Cl (4-) |
| 4-CF₃ | H | O | H | H | H | H | -C₆H₄-CF₃ (4-) |
| 4-CF₃ | H | O | H | H | H | H | -C₆H₄-OCF₃ (4-) |
| H | H | O | H | H | H | H | -C₆H₄-CF₃ (4-) |
| 4-t.-butyl | H | O | H | H | H | H | -C₆H₄-CF₃ (4-) |
| 3-CF₃ | H | O | H | H | H | H | -C₆H₄-OCF₃ (4-) |
| 4-CH₃ | H | O | H | H | H | H | -C₆H₄-CF₃ (4-) |
| 4-CH₃ | H | O | H | H | H | H | -C₆H₄-Cl (4-) |

TABLE 1D-continued

| Y | Z | X | R² | R³ | R⁴ | R⁵ | R⁶ |
|---|---|---|----|----|----|----|----|
| 4-Cl | H | O | H | H | H | H | ![4-Br-phenyl] |
| 4-Cl | H | O | H | H | H | H | ![4-CF₃-phenyl] |
| 4-F | H | O | H | H | H | H | ![4-OCF₃-phenyl] |
| 4-Cl | H | O | H | CH₃ | H | H | ![4-CF₃-phenyl] |
| 4-OCHF₂ | H | O | H | CH₃ | H | H | ![4-OCF₃-phenyl] |
| 4-F | H | O | H | CH₃ | CH₃ | H | ![4-CF₃-phenyl] |
| 4-CF₃ | H | O | H | H | H | H | ![3-F, 4-CF₃-phenyl] |
| 4-Cl | H | O | H | H | H | H | ![4-Cl-phenyl] |
| 4-Br | H | O | H | H | H | H | ![4-OCF₃-phenyl] |
| 4-Cl | H | O | H | H | H | H | ![4-CF₃-cyclohexyl] |

TABLE 1E
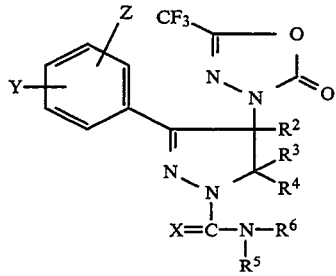
| Y | Z | X | R² | R³ | R⁴ | R⁵ | R⁶ |
|---|---|---|----|----|----|----|----|
| H | H | O | H | H | H | H | 4-CF₃-C₆H₄ |
| H | H | O | H | H | H | H | 4-OCF₃-C₆H₄ |
| 4-CF₃ | H | O | H | H | H | H | 4-CF₃-C₆H₄ |
| 4-CF₃ | H | O | H | H | H | H | 4-Cl-C₆H₄ |
| 4-CF₃ | H | O | H | H | H | H | 4-OCF₃-C₆H₄ |
| 4-Br | H | O | H | H | H | H | 4-CF₃-C₆H₄ |
| 3-CF₃ | H | O | H | H | H | H | 4-Cl-C₆H₄ |
| 3-CF₃ | H | O | H | H | H | H | 4-OCHF₂-C₆H₄ |
| 4-F | H | O | H | H | H | H | 4-Cl-C₆H₄ |
| 4-F | H | O | H | H | H | H | 4-CF₃-C₆H₄ |
| 4-F | H | O | H | H | H | H | 4-OCF₃-C₆H₄ |

TABLE 1E-continued

| Y | Z | X | R² | R³ | R⁴ | R⁵ | R⁶ |
|---|---|---|---|---|---|---|---|
| 4-F | H | O | H | H | H | H | -C₆H₄-OCHF₂ (4-) |
| 4-F | H | O | H | H | H | H | -C₆H₄-SCF₃ (4-) |
| 4-F | H | O | H | H | H | H | -C₆H₄-OCF₂—CHF₂ (4-) |
| 4-F | H | O | H | H | H | H | -C₆H₄-CHF₂ (4-) |
| 4-F | H | O | H | H | H | H | -C₆H₄-F (4-) |
| 4-Cl | H | O | H | H | H | H | -C₆H₄-CF₃ (4-) |
| 4-OCHF₂ | H | O | H | H | H | H | -C₆H₄-OCF₃ (4-) |
| 4-F | H | S | H | H | H | H | -C₆H₄-CF₃ (4-) |
| 4-F | H | O | CH₃ | H | H | H | -C₆H₄-Cl (4-) |
| 4-F | H | O | COOCH₃ | H | H | H | -C₆H₄-OCF₃ (4-) |
| 4-F | H | O | H | CH₃ | H | H | -C₆H₄-SCF₃ (4-) |

TABLE 1E-continued

[Structure diagram showing pyrazoline with Y/Z-substituted phenyl, CF3-containing oxadiazolone, and X=C-N(R5)R6 substituents]

| Y | Z | X | R² | R³ | R⁴ | R⁵ | R⁶ |
|---|---|---|----|----|----|----|----|
| 4-F | H | S | H | H | H | H | –C₆H₄–OCHF₂ (4-) |
| 4-Cl | 3-Cl | O | H | H | H | H | –C₆H₁₀(H)–CF₃ (cyclohexyl, 4-CF₃) |
| 4-Cl | H | O | H | H | H | H | –C₆H₄–OCF₃ (4-) |
| 4-Cl | H | O | H | H | H | H | –C₆H₄–OCHF₂ (4-) |
| 4-Cl | H | O | H | H | H | H | –C₆H₃(–O–CF₂–CF₂–O–) (benzodioxole, tetrafluoro) |
| 4-OCHF₂ | H | O | H | H | H | H | –C₆H₄–CF₃ (4-) |
| 4-OCHF₂ | H | O | H | H | H | H | –C₆H₄–OCF₃ (4-) |

TABLE 1F

[Structure: phenyl group with Y and Z substituents attached to a pyrazoline ring system bearing Br, N-CH3, C=O, R2, R3, R4 groups and X=C-N(R5)(R6) substituent]

| Y | Z | X | R² | R³ | R⁴ | R⁵ | R⁶ |
|---|---|---|----|----|----|----|----|
| 4-OCHF₂ | H | O | H | H | H | H | —C₆H₄—Cl (4-Cl) |
| 4-OCHF₂ | H | O | H | H | H | H | —C₆H₄—OCF₂—CHF₂ (4-) |
| 4-OCH₂CF₃ | H | O | H | H | H | H | —C₆H₄—CF₃ (4-) |
| 4-OCH₂CF₃ | H | O | H | H | H | H | —C₆H₄—Cl (4-) |
| 4-CF₃ | H | O | H | H | H | H | —C₆H₄—CF₃ (4-) |
| 4-CF₃ | H | O | H | H | H | H | —C₆H₄—OCF₃ (4-) |
| H | H | O | H | H | H | H | —C₆H₄—CF₃ (4-) |
| 4-t.-butyl | H | O | H | H | H | H | —C₆H₄—CF₃ (4-) |
| 3-CF₃ | H | O | H | H | H | H | —C₆H₄—OCF₃ (4-) |
| 4-CH₃ | H | O | H | H | H | H | —C₆H₄—CF₃ (4-) |
| 4-CH₃ | H | O | H | H | H | H | —C₆H₄—Cl (4-) |

TABLE 1F-continued
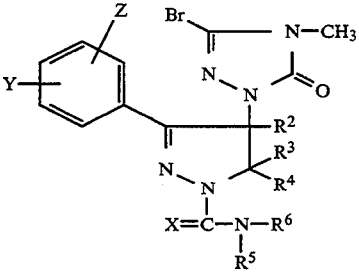
| Y | Z | X | R² | R³ | R⁴ | R⁵ | R⁶ |
|---|---|---|----|----|----|----|----|
| 4-Cl | H | O | H | H | H | H | 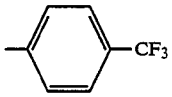 |
| 4-Cl | H | O | H | H | H | H | 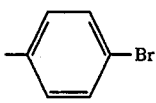 |
| 4-F | H | O | H | H | H | H | 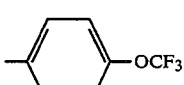 |
| 4-Cl | H | O | H | CH₃ | H | H | 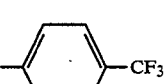 |
| 4-OCHF₂ | H | O | H | CH₃ | H | H | 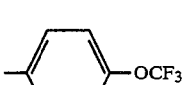 |
| 4-F | H | O | H | CH₃ | CH₃ | H | 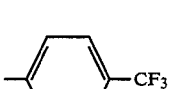 |
| 4-CF₃ | H | O | H | H | H | H | 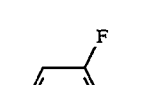 |
| 4-Cl | H | O | H | H | H | H |  |
| 4-Br | H | O | H | H | H | H |  |
| 4-Cl | H | O | H | H | H | H |  |

TABLE 1G

| Y | Z | X | R² | R³ | R⁴ | R⁵ | R⁶ |
|---|---|---|----|----|----|----|----|
| H | H | O | H | H | H | H | —C₆H₄—CF₃ (4-) |
| H | H | O | H | H | H | H | —C₆H₄—OCF₃ (4-) |
| 4-CF₃ | H | O | H | H | H | H | —C₆H₄—CF₃ (4-) |
| 4-CF₃ | H | O | H | H | H | H | —C₆H₄—Cl (4-) |
| 4-CF₃ | H | O | H | H | H | H | —C₆H₄—OCF₃ (4-) |
| 4-Br | H | O | H | H | H | H | —C₆H₄—CF₃ (4-) |
| 3-CF₃ | H | O | H | H | H | H | —C₆H₄—Cl (4-) |
| 3-CF₃ | H | O | H | H | H | H | —C₆H₄—OCHF₂ (4-) |
| 4-F | H | O | H | H | H | H | —C₆H₄—Cl (4-) |
| 4-F | H | O | H | H | H | H | —C₆H₄—CF₃ (4-) |
| 4-F | H | O | H | H | H | H | —C₆H₄—OCF₃ (4-) |
| 4-F | H | O | H | H | H | H | —C₆H₄—OCHF₂ (4-) |
| 4-F | n | O | H | H | H | H | —C₆H₄—SCF₃ (4-) |
| 4-F | H | O | H | H | H | H | —C₆H₄—OCF₂—CHF₂ (4-) |
| 4-F | H | O | H | H | H | H | —C₆H₄—CHF₂ (4-) |
| 4-F | H | O | H | H | H | H | —C₆H₄—F (4-) |
| 4-Cl | H | O | H | H | H | H | —C₆H₄—CF₃ (4-) |
| 4-OCHF₂ | H | O | H | H | H | H | —C₆H₄—OCF₃ (4-) |
| 4-F | H | S | H | H | H | H | —C₆H₄—CF₃ (4-) |

TABLE 1H

[Structure diagram: pyrazole compound with Y, Z substituents on phenyl, R², R³, R⁴ on pyrazoline ring, X=C-N(R⁵)(R⁶)]

| Y | Z | X | R² | R³ | R⁴ | R⁵ | R⁶ |
|---|---|---|---|---|---|---|---|
| 4-F | H | O | CH₃ | H | H | H | 4-Cl-phenyl |
| 4-F | H | O | COOCH₃ | H | H | H | 4-OCF₃-phenyl |
| 4-F | H | O | H | H | H | H | 4-SCF₃-cyclohexyl |
| 4-F | H | O | H | CH₃ | H | H | 4-OCHF₂-phenyl |
| 4-Cl | 3-Cl | O | H | H | H | H | 4-CF₃-phenyl |
| 4-Cl | H | O | H | H | H | H | 4-OCF₃-phenyl |
| 4-Cl | H | O | H | H | H | H | 4-OCHF₂-phenyl |
| 4-Cl | H | O | H | H | H | H | 2,3-(OCF₂CF₂O)-phenyl |
| 4-OCHF₂ | H | O | H | H | H | H | 4-CF₃-phenyl |
| 4-OCHF₂ | H | O | H | H | H | H | 4-OCF₃-phenyl |

TABLE 1H-continued

[Structure: pyrazole derivative with Y, Z substituents on phenyl ring, CH₃ on pyrazolone, R², R³, R⁴ substituents, and X=C-N(R⁵)(R⁶) group]

| Y | Z | X | R² | R³ | R⁴ | R⁵ | R⁶ |
|---|---|---|----|----|----|----|----|
| 4-OCHF₂ | H | O | H | H | H | H | 4-Cl-phenyl |
| 4-OCHF₂ | H | O | H | H | H | H | 4-(OCF₂-CHF₂)-phenyl |
| 4-OCH₂CF₃ | H | O | H | H | H | H | 4-CF₃-phenyl |
| 4-OCH₂CF₃ | H | O | H | H | H | H | 4-Cl-phenyl |
| 4-CF₃ | H | O | H | H | H | H | 4-CF₃-phenyl |
| 4-CF₃ | H | O | H | H | H | H | 4-OCF₃-phenyl |
| H | H | O | H | H | H | H | 4-CF₃-phenyl |
| 4-t.-butyl | H | O | H | H | H | H | 4-CF₃-phenyl |
| 3-CF₃ | H | O | H | H | H | H | 4-OCF₃-phenyl |
| 4-CH₃ | H | O | H | H | H | H | 4-CF₃-phenyl |
| 4-SCH₃ | H | O | H | H | H | H | 4-Cl-phenyl |

TABLE 1H-continued

[Structure: pyrazoline core with Y/Z-substituted phenyl, methylpyrazolone, R²/R³/R⁴ substituents, and X=C-N(R⁵)(R⁶) group]

| Y | Z | X | R² | R³ | R⁴ | R⁵ | R⁶ |
|---|---|---|----|----|----|----|----|
| 4-Br | H | O | H | H | H | H | 4-Br-C₆H₄ |
| 4-Cl | H | O | H | H | H | H | 4-CF₃-C₆H₄ |
| 4-F | H | O | H | H | H | H | 4-OCF₃-C₆H₄ |
| 4-Cl | H | O | H | CH₃ | H | H | 4-CF₃-C₆H₄ |
| 4-OCHF₂ | H | O | H | CH₃ | H | H | 4-OCF₃-C₆H₄ |
| 4-F | H | O | H | CH₃ | CH₃ | H | 4-CF₃-C₆H₄ |
| 4-CF₃ | H | O | H | H | H | H | 2-F-4-CF₃-C₆H₃ |
| 4-Cl | H | O | H | H | H | H | 4-Cl-C₆H₄ |
| 4-Br | H | O | H | H | H | H | 4-OCF₃-C₆H₄ |
| 4-F | H | O | H | H | H | H | 4-CF₃-cyclohexyl |

TABLE 1I

[Structure: pyrazole derivative with Y, Z substituents on phenyl, C₂H₅ group, R², R³, R⁴ substituents, and X=C-N(R⁵)(R⁶) group]

| Y | Z | X | R² | R³ | R⁴ | R⁵ | R⁶ |
|---|---|---|----|----|----|----|-----|
| H | H | O | H | H | H | H | 4-CF₃-phenyl |
| H | H | O | H | H | H | H | 4-OCF₃-phenyl |
| 4-CF₃ | H | O | H | H | H | H | 4-CF₃-phenyl |
| 4-CF₃ | H | O | H | H | H | H | 4-Cl-phenyl |
| 4-CF₃ | H | O | H | H | H | H | 4-OCF₃-phenyl |
| 4-Br | H | O | H | H | H | H | 4-CF₃-phenyl |
| 3-CF₃ | H | O | H | H | H | H | 4-Cl-phenyl |
| 3-CF₃ | H | O | H | H | H | H | 4-OCHF₂-phenyl |
| 4-F | H | O | H | H | H | H | 4-Cl-phenyl |
| 4-F | H | O | H | H | H | H | 4-Br-phenyl |
| 4-F | H | O | H | H | H | H | 4-OCF₃-phenyl |

TABLE 1I-continued

| Y | Z | X | R² | R³ | R⁴ | R⁵ | R⁶ |
|---|---|---|----|----|----|----|-----|
| 4-F | H | O | H | H | H | H | ―⟨C₆H₄⟩―OCHF₂ |
| 4-F | H | O | H | H | H | H | ―⟨C₆H₄⟩―SCF₃ |
| 4-F | H | O | H | H | H | H | ―⟨C₆H₄⟩―OCF₂―CHF₂ |
| 4-F | H | O | H | H | H | H | ―⟨C₆H₄⟩―CHF₂ |
| 4-F | H | O | H | H | H | H | ―⟨C₆H₄⟩―F |
| 4-Cl | H | O | H | H | H | H | ―⟨C₆H₄⟩―CF₃ |
| 4-OCHF₂ | H | O | H | H | H | H | ―⟨C₆H₄⟩―OCF₃ |
| 4-F | H | O | H | H | H | H | ―⟨C₆H₄⟩―CF₃ |
| 3,4-O―CF₂―O― | | O | H | H | H | H | ―⟨C₆H₄⟩―Cl |
| 4-Cl | H | O | H | H | H | H | ―⟨C₆H₁₀⟩―CF₃ (H) |
| 4-F | H | O | H | H | H | H | ―⟨C₆H₄⟩―CHF₂ |

TABLE 1I-continued

| Y | Z | X | R² | R³ | R⁴ | R⁵ | R⁶ |
|---|---|---|---|---|---|---|---|
| 4-F | H | O | H | H | H | H | 4-(OCF₂Cl)-phenyl |
| 4-Cl | H | O | —COOCH₃ | H | H | H | 4-(CF₃)-phenyl |
| 4-Cl | H | O | H | H | H | H | 4-(OCF₃)-phenyl |
| 4-Cl | H | O | H | H | H | H | 4-(OCHF₂)-phenyl |
| 4-Cl | H | O | H | H | H | H | 3,4-(OCF₂CF₂O)-phenyl |
| 4-OCHF₂ | H | O | H | H | H | H | 4-(CF₃)-phenyl |
| 4-OCHF₂ | H | O | H | H | H | H | 4-(OCF₃)-phenyl |

TABLE 1K
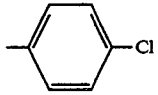
| Y | Z | X | R² | R³ | R⁴ | R⁵ | R⁶ |
|---|---|---|----|----|----|----|----|
| 4-OCHF₂ | H | O | H | H | H | H | 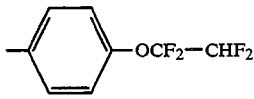 |
| 4-OCHF₂ | H | O | H | H | H | H | 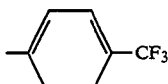 |
| 4-OCH₂CF₃ | H | O | H | H | H | H | 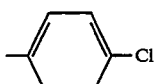 |
| 4-OCH₂CF₃ | H | O | H | H | H | H | 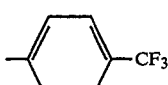 |
| 4-CF₃ | H | O | H | H | H | H | 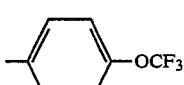 |
| 4-CF₃ | H | O | H | H | H | H | 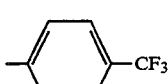 |
| H | H | O | H | H | H | H | 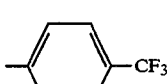 |
| 4-t.-butyl | H | O | H | H | H | H | 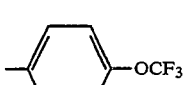 |
| 3-CF₃ | H | O | H | H | H | H | 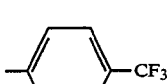 |
| 4-CH₃ | H | O | H | H | H | H | 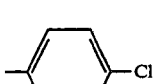 |
| 4-CH₃ | H | O | H | H | H | H | (4-Cl-phenyl) |

TABLE 1K-continued

| Y | Z | X | R² | R³ | R⁴ | R⁵ | R⁶ |
|---|---|---|----|----|----|----|----|
| 4-Cl | H | O | H | H | H | H | —C₆H₄—CF₃ (4-) |
| 4-Cl | H | O | H | H | H | H | —C₆H₄—Br (4-) |
| 4-F | H | O | H | H | H | H | —C₆H₄—OCF₃ (4-) |
| 4-Cl | H | O | H | CH₃ | H | H | —C₆H₄—CF₃ (4-) |
| 4-OCHF₂ | H | O | H | CH₃ | H | H | —C₆H₄—OCF₃ (4-) |
| 4-F | H | O | H | CH₃ | CH₃ | H | —C₆H₄—CF₃ (4-) |
| 4-CF₃ | H | O | H | H | H | H | —C₆H₃(3-F)(4-CF₃) |
| 4-Cl | H | O | H | H | H | H | —C₆H₄—Cl (4-) |
| 4-Br | H | O | H | H | H | H | —C₆H₄—OCF₃ (4-) |
| 4-Cl | H | O | H | H | H | H | —C₆H₁₀—CF₃ (4-, cyclohexyl) |

TABLE 1L
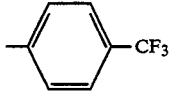
| Y | Z | X | R² | R³ | R⁴ | R⁵ | R⁶ |
|---|---|---|----|----|----|----|----|
| H | H | O | H | H | H | H | 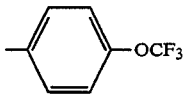 -C₆H₄-CF₃ |
| H | H | O | H | H | H | H | -C₆H₄-OCF₃ |
| 4-CF₃ | H | O | H | H | H | H | -C₆H₄-CF₃ |
| 4-CF₃ | H | O | H | H | H | H | -C₆H₄-Cl |
| 4-CF₃ | H | O | H | H | H | H | -C₆H₄-OCF₃ |
| 4-Br | H | O | H | H | H | H | -C₆H₄-CF₃ |
| 3-CF₃ | H | O | H | H | H | H | -C₆H₄-Cl |
| 3-CF₃ | H | O | H | H | H | H | -C₆H₄-OCHF₂ |
| 4-F | H | O | H | H | H | H | -C₆H₄-Cl |
| 4-F | H | O | H | H | H | H | -C₆H₄-CF₃ |
| 4-F | H | O | H | H | H | H | -C₆H₄-OCF₃ |

TABLE 1L-continued
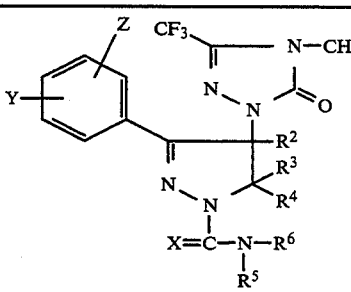
| Y | Z | X | R² | R³ | R⁴ | R⁵ | R⁶ |
|---|---|---|----|----|----|----|----|
| 4-F | H | O | H | H | H | H | 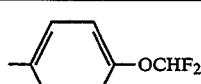 —⟨ ⟩—OCHF₂ |
| 4-F | H | O | H | H | H | H | 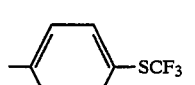 —⟨ ⟩—SCF₃ |
| 4-F | H | O | H | H | H | H | 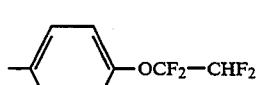 —⟨ ⟩—OCF₂—CHF₂ |
| 4-F | H | O | H | H | H | H | 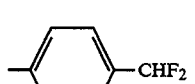 —⟨ ⟩—CHF₂ |
| 4-F | H | O | H | H | H | H | 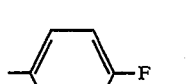 —⟨ ⟩—F |
| 4-Cl | H | O | H | H | H | H | 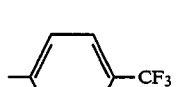 —⟨ ⟩—CF₃ |
| 4-OCHF₂ | H | O | H | H | H | H | 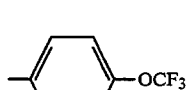 —⟨ ⟩—OCF₃ |
| 4-F | H | O | —CH₃ | H | H | H | 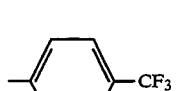 —⟨ ⟩—CF₃ |
| 4-O—(CH₂)₂—CH₃ | H | O | H | H | H | H | 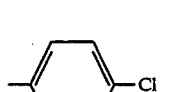 —⟨ ⟩—Cl |
| 4-F | H | O | CH₃ | H | H | H | 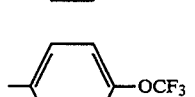 —⟨ ⟩—OCF₃ |
| 4-F | H | O | COOCH₃ | H | H | H |  —⟨ ⟩—SCF₃ |

TABLE 1L-continued

[Structure diagram showing pyrazoline with Y, Z on phenyl ring, CF₃, N-CH₃, R², R³, R⁴, X=C, N-R⁵, R⁶ substituents]

| Y | Z | X | R² | R³ | R⁴ | R⁵ | R⁶ |
|---|---|---|----|----|----|----|----|
| 4-F | H | O | H | H | H | H | 4-Br-phenyl |
| 4-Cl | H | O | H | H | H | H | 3-F-4-CF₃-phenyl |
| 4-Cl | H | O | H | H | H | H | 4-Br-phenyl |
| 4-Cl | H | O | H | H | H | H | 4-OCF₂Cl-phenyl |
| 4-Cl | H | O | H | H | H | H | 3,4-(OCF₂CF₂O)-phenyl |
| 4-OCHF₂ | H | S | H | H | H | H | 4-CF₃-phenyl |
| 4-OCHF₂ | H | O | H | H | H | H | 4-OCF₃-phenyl |
| 4-OCHF₂ | H | O | H | H | H | H | 4-Cl-phenyl |
| 4-OCHF₂ | H | O | H | H | H | H | 4-OCF₂-CHF₂-phenyl |
| 4-OCH₂CF₃ | H | O | H | H | H | H | 4-CF₃-phenyl |

TABLE 1L-continued
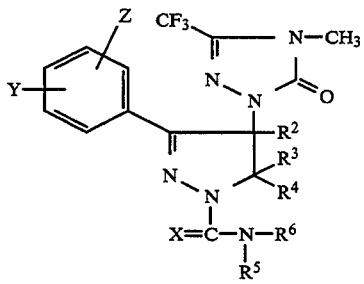
| Y | Z | X | R² | R³ | R⁴ | R⁵ | R⁶ |
|---|---|---|----|----|----|----|----|
| 4-OCH₂CF₃ | H | O | H | H | H | H |  4-Cl-C₆H₄ |
| 4-Br | H | O | H | H | H | H | 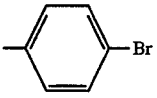 4-Br-C₆H₄ |
| 4-Cl | H | O | H | H | H | H | 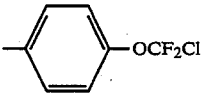 4-OCF₂Cl-C₆H₄ |
| H | H | O | H | H | H | H | 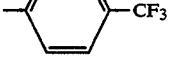 4-CF₃-C₆H₄ |
| 4-t.-butyl | H | O | H | H | H | H | 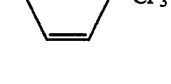 4-CF₃-C₆H₄ |
| 3-CF₃ | H | O | H | H | H | H | 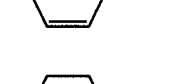 4-OCF₃-C₆H₄ |
| 4-CH₃ | H | O | H | H | H | H |  4-CF₃-C₆H₄ |
| 4-CH₃ | H | O | H | H | H | H |  4-Cl-C₆H₄ |
| 4-Cl | H | O | H | CH₃ | H | H | 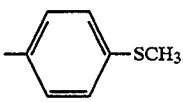 4-CF₃-C₆H₄ |
| 4-Cl | H | O | H | H | H | H | 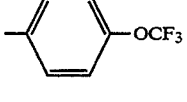 4-SCH₃-C₆H₄ |
| 4-Br | H | O | H | H | H | H |  4-OCF₃-C₆H₄ |

TABLE 1L-continued

| Y | Z | X | R² | R³ | R⁴ | R⁵ | R⁶ |
|---|---|---|----|----|----|----|----|
| 4-O—(CH₂)₂—CH₃ | H | O | H | CH₃ | H | H | 4-CF₃-phenyl |
| 4-OCHF₂ | H | O | H | CH₃ | H | H | 4-OCF₃-phenyl |
| 4-F | H | O | H | CH₃ | CH₃ | H | 4-CF₃-phenyl |
| 4-CF₃ | H | O | H | H | H | H | 3-F-4-CF₃-phenyl |
| 4-Cl | H | O | H | H | H | H | 4-Cl-phenyl |
| 4-Cl | H | O | H | H | H | H | 4-CF₃-cyclohexyl |

TABLE M

| Y | Z | X | R² | R³ | R⁴ | R⁵ | R⁶ |
|---|---|---|----|----|----|----|----|
| H | H | O | H | H | H | H | 4-CF₃-phenyl |
| H | H | O | H | H | H | H | 4-OCF₃-phenyl |

TABLE M-continued
| | | | | | | | |
|---|---|---|---|---|---|---|---|
| 4-CF₃ | H | O | H | H | H | H | 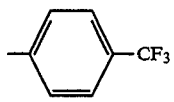 |
| H | H | O | H | H | H | H | 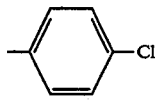 |
| 4-CF₃ | H | O | H | H | H | H | 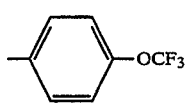 |
| 4-Br | H | O | H | H | H | H | 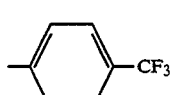 |
| 3-CF₃ | H | O | H | H | H | H | 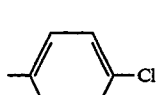 |
| 3-CF₃ | H | O | H | H | H | H | 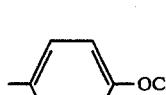 |
| 4-F | H | O | H | H | H | H | 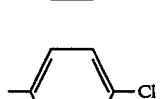 |
| 4-F | H | O | H | H | H | H | 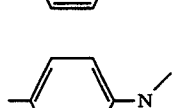 |
| 4-F | H | O | H | H | H | H | 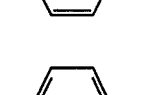 |
| 4-F | H | O | H | H | H | H | 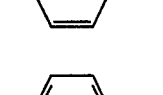 |
| 4-F | H | O | H | H | H | H | 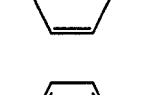 |
| 4-F | H | O | H | H | H | H | 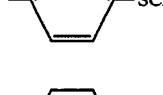 |
| 4-F | H | O | H | H | H | H | 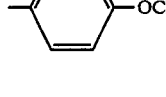 |

TABLE M-continued
| | | | | | | | |
|---|---|---|---|---|---|---|---|
| 4-F | H | O | H | H | H | | 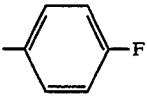 |
| 4-Cl | H | O | H | H | H | | 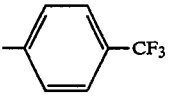 |
| 4-OCHF$_2$ | H | O | H | H | H | | 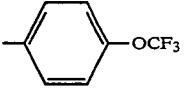 |
| 4-F | H | O | H | H | H | | 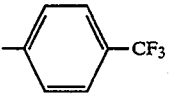 |
| 4-Br | H | O | H | H | H | | 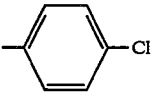 |
| 4-F | H | O | H | H | —CH$_3$ | | 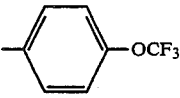 |
| 4-Br | H | O | H | H | H | | 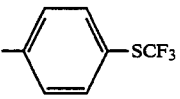 |
| 4-F | H | O | H | H | H | | 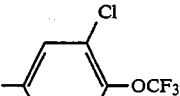 |
| 4-Cl | H | O | H | H | H | | 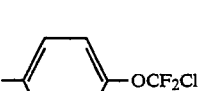 |
| 4-Cl | H | O | H | H | H | | 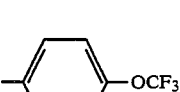 |
| 4-Cl | H | O | H | H | H | |  |
| 4-Cl | H | O | H | H | H | |  |
| 4-OCHF$_2$ | H | O | H | H | H | | 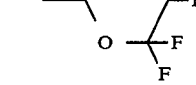 |

TABLE M-continued
| | | | | | | | |
|---|---|---|---|---|---|---|---|
| 4-OCHF$_2$ | H | O | H | H | H | H | 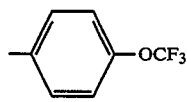 |
| 4-OCHF$_2$ | H | O | H | H | H | H | 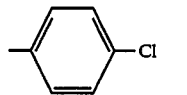 |
| 4-OCHF$_2$ | H | O | H | H | H | H | 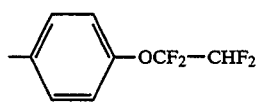 |
| 4-OCH$_2$CF$_3$ | H | O | H | H | H | H | 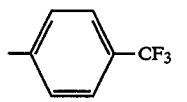 |
| 4-OCH$_2$CF$_3$ | H | O | H | H | H | H | 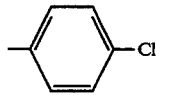 |
| 4-CF$_3$ | H | O | H | H | H | H | 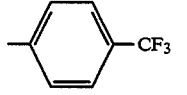 |
| 4-CF$_3$ | H | O | H | H | H | H | 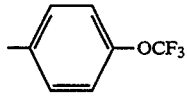 |
| 4-O—CH$_2$—CH$_3$ | H | O | H | H | H | H | 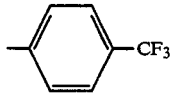 |
| 4-t.-butyl | H | O | H | H | H | H | 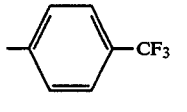 |
| 3-CF$_3$ | H | O | H | H | H | H | 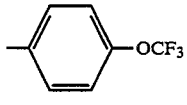 |
| 4-CH$_3$ | H | O | H | H | H | H | 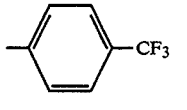 |
| 4-CH$_3$ | H | O | H | H | H | H | 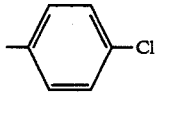 |
| —O—(CH$_2$)$_2$—CH$_3$ | H | O | H | H | H | H | 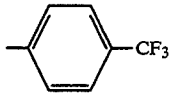 |

TABLE M-continued
| Y | Z | X | R² | R³ | R⁴ | R⁵ | R⁶ |
|---|---|---|----|----|----|----|----|
| 4-Cl | H | O | H | H | H | H | 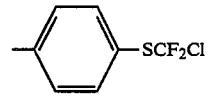 |
| 4-F | H | O | H | H | H | H | 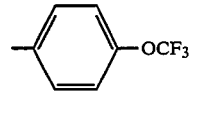 |
| 4-Cl | H | O | H | CH₃ | H | H | 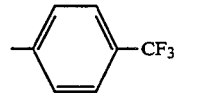 |
| 4-OCHF₂ | H | O | H | CH₃ | H | H | 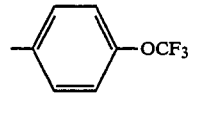 |
| 4-F | H | O | H | CH₃ | CH₃ | H | 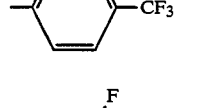 |
| 4-CF₃ | H | O | H | H | H | H | 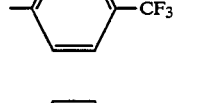 |
| 4-Cl | H | O | H | H | H | H | 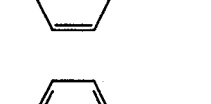 |
| 4-Br | H | O | H | H | H | H | 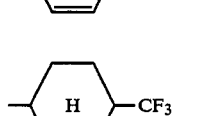 |
| 4-Cl | H | O | H | H | H | H |  |
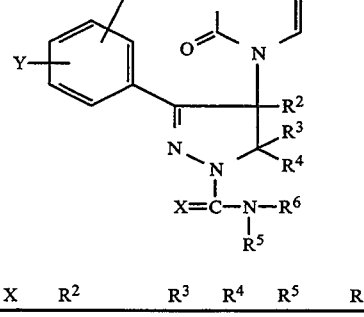
| Y | Z | X | R² | R³ | R⁴ | R⁵ | R⁶ |
|---|---|---|----|----|----|----|----|
| 4-CF₃ | H | O | H | H | H | H | 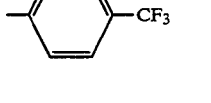 |

TABLE M-continued
| | | | | | | | |
|---|---|---|---|---|---|---|---|
| 4-CF₃ | H | O | H | H | H | H | 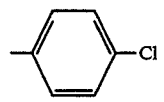 |
| 4-CF₃ | H | O | H | H | H | H | 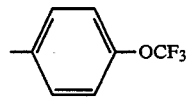 |
| 4-Br | H | O | H | H | H | H | 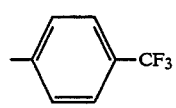 |
| 3-CF₃ | H | O | H | H | H | H | 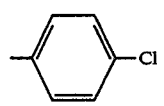 |
| 3-CF₃ | H | O | H | H | H | H | 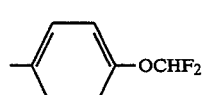 |
| 4-F | H | O | H | H | H | H | 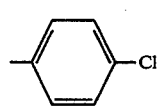 |
| 4-F | H | O | H | H | H | H | 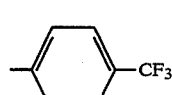 |
| 4-F | H | O | H | H | H | H | 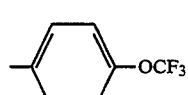 |
| 4-F | H | O | H | H | H | H | 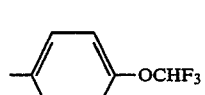 |
| 4-F | H | O | H | H | H | H | 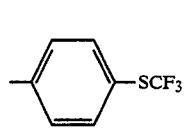 |
| H | H | O | H | H | H | H | 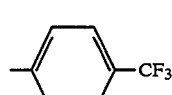 |
| H | H | O | H | H | H | H | 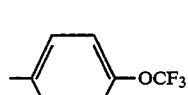 |
| 4-F | H | O | H | H | H | H | 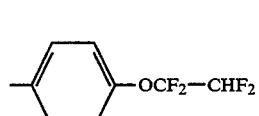 |

TABLE M-continued

| | | | | | | |
|---|---|---|---|---|---|---|
| 4-F | H | O | H | H | H | —C₆H₄—CHF₂ (para) |
| 4-F | H | O | H | H | H | —C₆H₄—F (para) |
| 4-Cl | H | O | H | H | H | —C₆H₄—CF₃ (para) |
| 4-OCHF₂ | H | O | H | H | H | —C₆H₄—OCF₃ (para) |
| 4-F | H | O | H | H | H | —C₆H₁₀—CF₃ (cyclohexyl, para) |
| 4-F | H | O | CH₃ | H | H | —C₆H₄—Cl (para) |
| 4-F | H | O | COOCH₃ | H | H | —C₆H₄—OCF₃ (para) |
| 4-F | H | O | H | CH₃ | H | —C₆H₄—SCF₃ (para) |
| 4-F | H | S | H | H | H | —C₆H₄—OCHF₂ (para) |
| 4-Cl | 3-Cl | O | H | H | H | —C₆H₁₀—CF₃ (cyclohexyl, para) |
| 4-Cl | H | O | H | H | H | —C₆H₄—OCF₃ (para) |
| 4-Cl | H | O | H | H | H | —C₆H₄—OCHF₂ (para) |
| 4-Cl | H | O | H | H | H | —C₆H₃(O—CF₂—CF₂—O) (3,4-dioxy-tetrafluoroethylene) |

TABLE M-continued

| | | | | | | | |
|---|---|---|---|---|---|---|---|
| 4-OCHF$_2$ | H | O | H | H | H | H | -C$_6$H$_4$-CF$_3$ |
| 4-OCHF$_2$ | H | O | H | H | H | H | -C$_6$H$_4$-OCF$_3$ |
| 4-OCHF$_2$ | H | O | H | H | H | H | -C$_6$H$_4$-Cl |
| 4-OCHF$_2$ | H | O | H | H | H | H | -C$_6$H$_4$-OCF$_2$—CHF$_2$ |
| 4-OCH$_2$CF$_3$ | H | O | H | H | H | H | -C$_6$H$_4$-CF$_3$ |
| 4-OCH$_2$CF$_3$ | H | O | H | H | H | H | -C$_6$H$_4$-Cl |
| 4-CF$_3$ | H | O | H | H | H | H | -C$_6$H$_{10}$(H)-CF$_3$ |
| 4-F | H | O | H | H | H | H | -C$_6$H$_4$-OCF$_2$Cl |
| 4-F | H | O | CH$_3$ | H | H | H | -C$_6$H$_4$-OCF$_3$ |
| 4-F | H | O | COOCH$_3$ | H | H | H | -C$_6$H$_4$-SCF$_3$ |
| 4-Cl | H | O | H | H | H | H | -C$_6$H$_3$(F)-CF$_3$ |

If, for example, 3-(4'-chlorophenyl)-4-(4''-methyl-3''-trifluoromethyl-Δ$^{2''}$-1'',2'',''4-triazolin-5''-on-1''-yl)-4,5-dihydropyrazole and 4-trifluoro-methoxy-phenyl isocyanate are used as starting materials, the course of the reaction of process (A) according to the invention can be represented by the following equation:

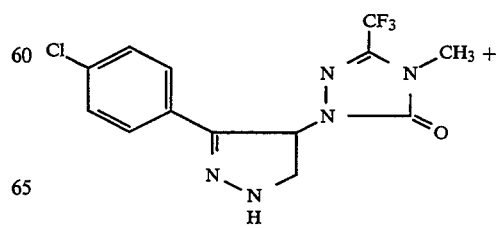

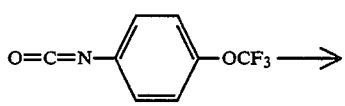

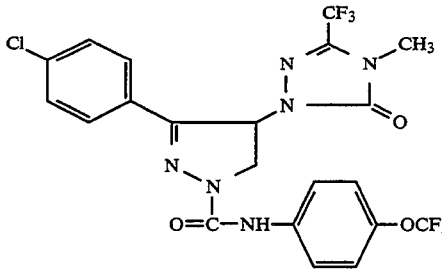

If, for example, N-(4-trifluoromethoxy)-3-(4'-chlorophenyl)-4-(4''-methyl-3''-trifluoromethyl-Δ$^{2''}$-1'',2'',4''-triazolin-5''-on-1''-yl)-4,5-dihydro-1-pyrazole-carboxanilide and 2-iodopropane are used as starting materials, the course of the reaction of process (B) according to the invention can be represented as follows:

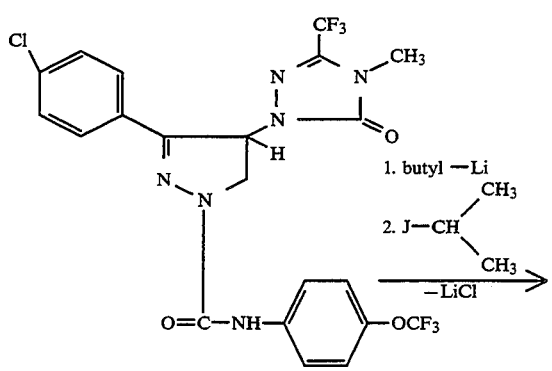

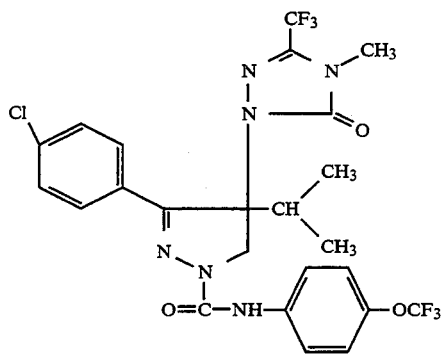

Formula (II) provides a general definition of the pyrazoline derivatives required as starting materials for carrying out the process (A) according to the invention. In this formula (II), R$^1$, R$^2$, R$^3$, R$^4$, Y and Z preferably represent those radicals which have already been mentioned in connection with the description of the substances of the formula (I) according to the invention as being preferred for these substituents. The pyrazoline derivatives of the formula (II) are new and can be prepared by one of the following processes.

They are prepared by reacting compounds of the formula (VI)

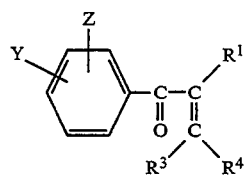

with hydrazine hydrate in a polar organic solvent, preferably an alkanol, at temperatures from 20° to 80° C., in particular at 30° to 60° C.:

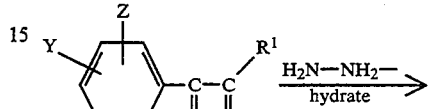

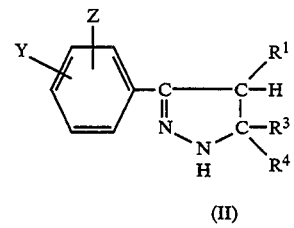

Depending on the meaning of the substituents R$^3$ and R$^4$, this results in the following process variants of the starting compounds of the formula (VI)

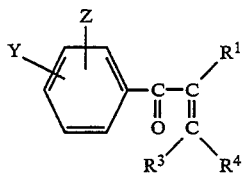

a) R$^3$ and R$^4$ in formula (VI) represent hydrogen

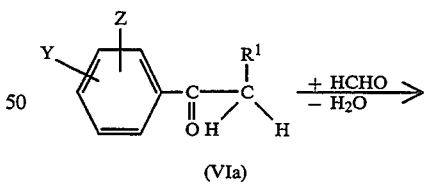

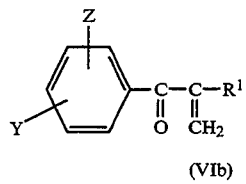

In this case, the reaction is carried out with a formalin solution in a polar organic solvent, preferably an alkanol and, in particular, in ethanol or methanol, with addition of small amounts of an organic base, in particular piperidine, and addition of glacial acetic acid.

b) In the formula (VI), R$^3$ represents alkyl or aryl and R$^4$ represents hydrogen:

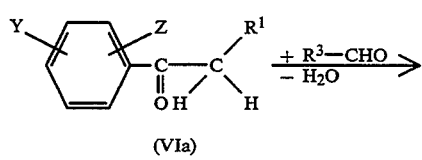

(VIa)

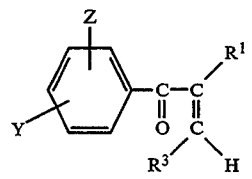

(VIc)

The process conditions correspond to those in the reaction with formaldehyde.

c) In the formula (VI), $R^3$ and $R^4$ represent alkyl:

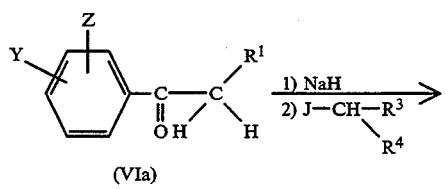

(VIa)

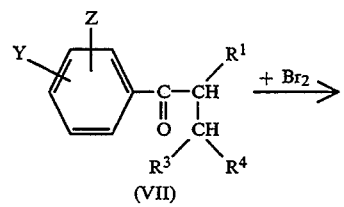

(VII)

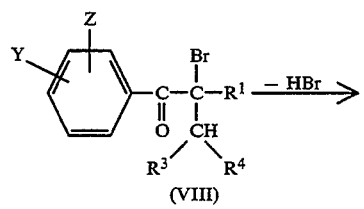

(VIII)

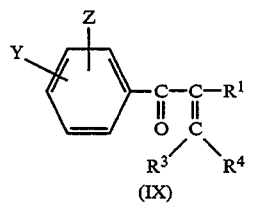

(IX)

In this case, the compound (VI) is first converted into the salt using a strong base, and the product is subsequently reacted with a halide, in particular an iodide of the formula

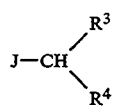

The compounds of the formula (VII) formed in this process is brominated, and the intermediate of the formula (IX) is subsequently prepared by adding a base and eliminating HBr.

Compounds of the formula (II) in which $R^3$ and $R^4$ represent hydrogen are furthermore obtained by reacting compounds of the formula (VId)

(VId)

in which

Y and Z have the abovementioned meaning and $R^{2-1}$ represents hydrogen, alkyl or alkoxycarbonyl, by first heating them, or, if appropriate, refluxing them, in a 1st step in a polar organic solvent, preferably acetonitrile, at temperatures from 10° to 100° C., in particular at 20° to 80° C., with one mole of N,N-dimethylmethyleneimmonium chloride of the formula (XI), $$CH_2=\overset{+}{N}(CH_3)_2 \ Cl^-$$ (XI)

and the intermediate of the formula (XII) which is formed

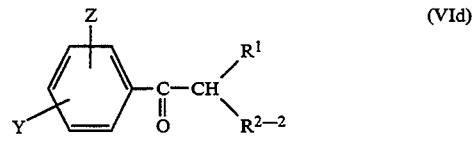

(XII)

is, if appropriate, isolated and subsequently, in a second step, cyclised with hydrazine hydrate in a polar organic solvent, preferably an alcohol, at temperatures from 20° to 80° C., in particular at 30° to 60° C., to give compounds of the formula (II).

Compounds of the formula (II) in which $R^3$ represents the radical $-CH_2-N(CH_3)_2$ and $R^4$ represents hydrogen are obtained by first heating, if appropriate refluxing, in a 1st step, compounds of the formula (VId)

(VId)

in which

Y and Z have the abovementioned meaning and $R^{2-1}$ represents hydrogen, alkyl or alkoxycarbonyl, with 2 mol of N,N-dimethylmethyleneimmonium chloride of the formula (XI), $$CH_2=\overset{+}{N}(CH_3)_2 \ Cl^-$$ (XI)

in a polar organic solvent, preferably acetonitrile, at temperatures from 10° to 100° C., in particular at 20° to 80° C., and the intermediate of the formula (XIIa) which is formed

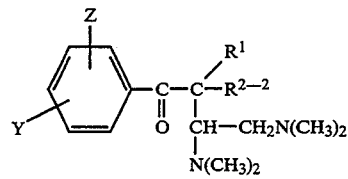

(XIIa)

is, if appropriate, isolated and subsequently, in a second step, cyclised with hydrazine hydrate in a polar organic solvent, preferably an alcohol, at temperatures from 20° to 80° C., in particular at 30° to 60° C., to give compounds of the formula (II) (cf. also the Preparation Example).

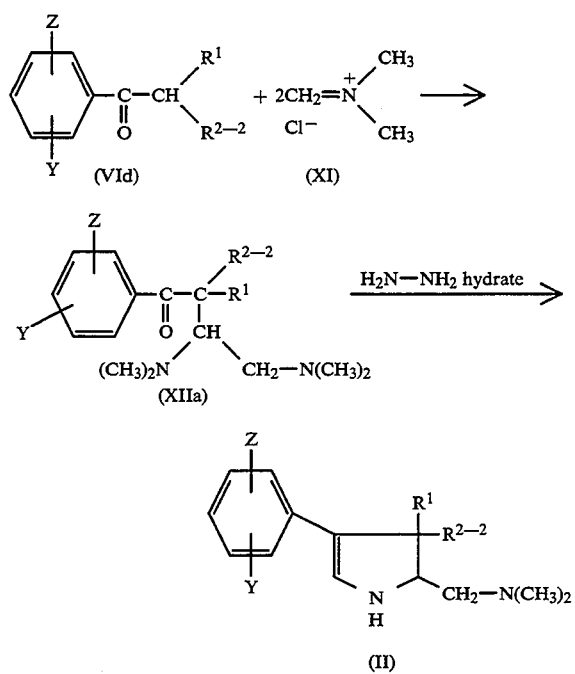

Some of the compounds of the formula (VIa) and (VId) are new. They are prepared by reacting the compounds

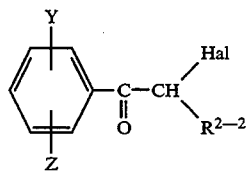

(X)

in which $R^{2-2}$ represents hydrogen, alkyl or alkoxycarbonyl,

X and Y have the abovementioned meaning and

Hal represents halogen, in particular bromine, with the compound $R^1$-H with the aid of an organic or inorganic base with the elimination of hydrogen halide. The compounds of the formula (X) and $R^1$-H are known substances (cf., for example, Comprehensive Heterocyclic Chemistry, A. R. Katritzky, Vol. 5, Part 4A, Pergamon Press and U.S. Pat. No. 3,780,052).

When carrying out the process according to the invention following the process variant ( B ), compounds of the formula (IV)

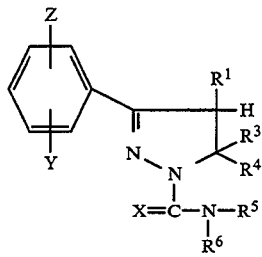

(IV)

in which X, Y, Z, $R^1$, $R^2$, $R^4$, $R^5$ and $R^6$ have the abovementioned meaning, are reacted with a strong base, preferably an organometal compound, in particular with butyl-lithium, in the inert organic solvent at temperatures from −50° to 0° C., in particular from −30° C. to −15° C., if appropriate in the presence of a protective-gas atmosphere, in particular a rare-gas atmosphere such as, for example, argon, and the product is subsequently reacted with a halide Hal-$R^2$ in which $R^{2-2}$ represents alkyl, optionally substituted cycloalkyl, halogenoalkyl, alkoxycarbonyl or halogenoalkylthio, at 0° to 60° C., in particular at −10° to −40° C., and the mixture is worked up in the customary manner by adding water and extracting the mixture with ether.

This gives compounds of the formula (XIII)

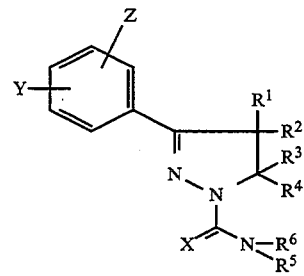

(XI)

in which X, Y, Z, $R^1$, $R^2$, $R^3$, $R^4$, $R^5$, $R^6$ and $R^9$ have the abovementioned meanings.

The active compounds are suitable for combating-animal pests, preferably arthropods and nematodes, in particular insects and arachnids, which occur in agriculture, in animal keeping, in forests, in the protection of stored products and of materials, and in the hygiene sector. They are active against normally sensitive and resistant species and against all or individual development stages.

The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus, Gryllotalpa spp.,*

*Locusta migratoria migratorioides, Melanoplus differentialis* and *Schistocerca gregaria.*

From the order of the Dermaptera, for example, *Forficula auricularia.*

From the order of the Isoptera, for example, *Reticulitermes spp.*

From the order of the Anoplura, for example, *Phylloxera vastatrix, Pemphigus spp., Pediculus humanus corporis, Haematopinus spp.* and *Linognathus spp.*

From the order of the Mallophaga, for example, *Trichodectes spp.* and *Damalinea spp.*

From the order of the Thysanoptera, for example, *Hercinothrips femoralis* and *Thrips tabaci.*

From the order of the Heteroptera, for example, *Eurygaster spp., Dysdercus intermedius, Piesma quadrata, Cimex lectularius, Rhodnius prolixus* and *Triatoma spp.*

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp. Psylla spp.*

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Agrotis spp., Euxoa spp., Feltia spp., Earias insulana, Heliothis spp., Spodoptera exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varive stis, Atomaria spp., Oryzaephilus surinamensis, Antho nomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbiumpsylloides, Tribolium spp., Tenebrio molitor, Agriotes spp., Cono derus spp., Melolontha melolontha, Amphimallon solsti tialis* and *Costelytra zealandica.*

From the order of the Hymenoptera, for example, *Diprion spp., Hoplocampa spp., Lasius spp., Monomoriumpharaonis* and *Vespa spp.*

From the order of the Diptera, for example, *Aedes spp., Anopheles spp., Culex spp., Drosophila melanogaster, Musca spp., Hydrotaea spp., Haematobia spp., Glossina spp., Melophagus spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa.*

From the order of the Siphonaptera, for example, *Xenopsylla cheopis, Ceratophyllus spp.* and *Ctenocephalides spp.*

From the order of the Arachnida for example *Scorpio maurus* and *Latrodectus mactans.*

From the order of the Acarina, for example, *Acarus siro, Argas spp., Ornithodoros spp., Dermanyssus gallinae, Ornithonyssus spp., Eriophyes ribis, Phyllocoptruta oleivora, Boophilus spp., Rhipicephalus spp., Amblyomma spp., Hyalomma spp., Ixodes spp., Dermacentor spp., Haemaphysalis spp., Otobius spp., Psoroptes spp., Chorioptes spp., Sarcoptes spp., Psorergates spp., Demodex spp., Notoedres spp., Tarsonemus spp., Bryobia praetiosa, Panonychus spp.* and *Tetranychus spp.*

The active compounds according to the invention are not only active against plant, hygiene and stored product pests, but also, in the veterinary medicine sector, against animal parasites (ectoparasites and endoparasites) such as scaly ticks, argasidae, scab mites, trombidae, flies (stinging and licking), parasitic fly larvae, lice, hair lice, bird lice, fleas and worms which live as endoparasites.

They are active against normally-sensitive and resistant species and strains as well against all parasitic and non-parasitic development stages of the ecto- and endoparasites.

The active compounds according to the invention are distinguished by a powerful insecticidal and acaricidal activity.

They can be employed particularly successfully against insects which are harmful to plants such as, for example, against the larvae of the mustard beetle (*Phaedon cochleariae*) or against the caterpillars of the cabbage moth (*Plutella maculipennis*) or against the tobacco budworm (*Heliothis virescens*).

Moreover, they can be employed particularly successfully for combating pests of warm-blooded species which live as parasites such as, for example, against blowfly larvae (Lucilia cuprina), against Musca domestica and against Periplaneta americana.

The active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and furthermore into formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated ali phatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc. The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, attractants, sterilising agents, acaricides, nematicides, fungicides, growth-regulating substances or herbicides. The insecticides include, for example, phosphates, carbamates, carboxylates, chlorinated hydrocarbons, phenylureas, substances produced by microorganisms and the like.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating insects, mites, ticks and the like in the field of animal keeping and livestock breeding, so that, by combating the pests, better results, for example higher milk yield, higher weight, more beautiful animal coat, longer life and the like, can be achieved.

In this field, the active compounds according to the invention are applied in a known manner, such as by external administration in the form of, for example, dipping, spraying, pouring-on, spotting-on and dusting, as well by parenteral administration, for example in the form of an injection, and furthermore by the feed-through method. Besides, application as shaped articles (collar, ear mark), and application in the form of the so-called environment treatment, are also possible.

The examples which follow describe the preparation and the use of active compounds according to the invention without imposing any limitation.

PREPARATION EXAMPLES

Example 1

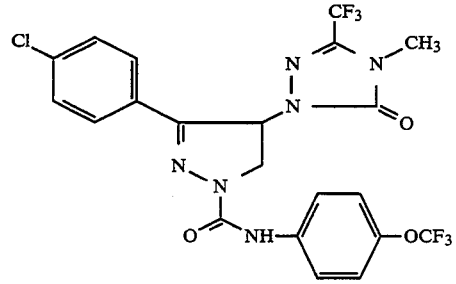

2.76 g (0,008 mol) of 3-(4'-chlorophenyl)-4-(4"-methyl-3"-trifluoromethyl-Δ2"-1",2",4"-triazolin-5"-on-1"-yl)-4,5-dihydropyrazole are dissolved in 20 ml of acetonitrile (anhydrous) at 60° C. until a clear solution has formed, this solution is treated with 1.7 g of 4-trifluoromethoxy-phenyl isocyanate, and 2drops of triethylamine are added. The mixture is subsequently allowed to stand for 2 hours at room temperature. The solvent is subsequently stripped off in vacuo, the residue is treated with 20 ml of diethyl ether and, after 2 hours, the precipitate which has formed is filtered off with suction. 2.0 g (45.6% of theory) of N-(4-trifluormethoxy)-3-(4'-chlorophenyl)-4-(4"-methyl-3"-trifluoromethyl-Δ2"-1",2",4,"-triazolin-5"-on-1"-yl)-4,5-dihydro-1-pyrazole-carboxanilide having a melting point of 241° C. are obtained.

The end products of the formula (I) which are listed below in Table 2 are obtained analogously to Example 1 and taking into consideration the information given in the description of the processes according to the invention:

TABLE 2

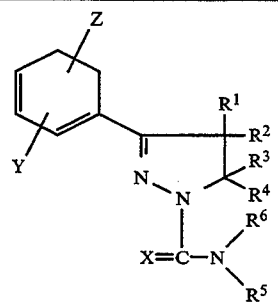
(I)

| Example No. | R¹ | R² | R³ | R⁴ | R⁵ | R⁶ | Y | Z | X | Melting point °C. |
|---|---|---|---|---|---|---|---|---|---|---|
| 2 | (1-methyl-5-methyl-3-oxo-1,2,4-triazol-4-yl) | H | H | H | H | 4-OCF₃-phenyl | 4Cl | H | O | 211 |
| 4 | (1-methyl-5-phenyl-3-oxo-1,2,4-triazol-4-yl) | H | H | H | H | 4-Cl-phenyl | 4Cl | H | O | 241 |
| 3 | (1-methyl-5-phenyl-3-oxo-1,2,4-triazol-4-yl) | H | H | H | H | 4-OCF₃-phenyl | 4Cl | H | O | 218 |
| 5 | (1-methyl-5-trifluoromethyl-3-oxo-1,2,4-triazol-4-yl) | H | H | H | H | 4-CF₃-phenyl | 4Cl | H | O | 230 |
| 6 | (1-methyl-5-trifluoromethyl-3-oxo-1,2,4-triazol-4-yl) | H | H | H | H | 4-Cl-phenyl | 4Cl | H | O | 256 |
| 7 | (1-methyl-5-trifluoromethyl-3-oxo-1,2,4-triazol-4-yl) | H | H | H | H | 4-Br-phenyl | 4Cl | H | O | 257 |
| 8 | (1-methyl-5-trifluoromethyl-3-oxo-1,2,4-triazol-4-yl) | H | H | H | H | 4-CF₃-cyclohexyl | 4Cl | H | O | 192 |
| 9 | (1-methyl-5-trifluoromethyl-3-oxo-1,2,4-triazol-4-yl) | H | H | H | H | 4-CClF₂-phenyl | 4Cl | H | O | 226 |
| 10 | (1-methyl-5-trifluoromethyl-3-oxo-1,2,4-triazol-4-yl) | H | H | H | H | 4-OCF₃-phenyl | H | H | O | 224 |

TABLE 2-continued

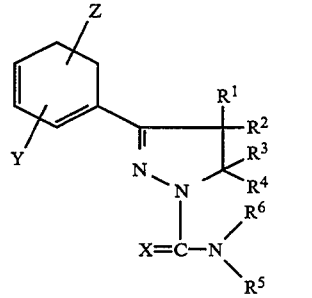
(I)

| Example No. | R¹ | R² | R³ | R⁴ | R⁵ | R⁶ | Y | Z | X | Melting point °C. |
|---|---|---|---|---|---|---|---|---|---|---|
| 11 | F₃C–C(=N-N(CH₃)-C(=O)-N–)– (methyl triazolinone with CF₃) | H | H | H | H | 4-CF₃-C₆H₄ | H | H | O | 238 |
| 12 | F₃C–(triazolinone-CH₃) | H | H | H | H | 4-Cl-C₆H₄ | H | H | O | 236 |
| 13 | F₃C–(triazolinone-CH₃) | H | H | H | H | 4-CClF₂-C₆H₄ | H | H | O | 204 |
| 14 | F₃C–(triazolinone-CH₃) | H | H | H | H | 4-SCF₂Cl-C₆H₄ | H | H | O | 221 |
| 15 | F₃C–(triazolinone-CH₃) | H | H | H | H | 4-SCF₃-C₆H₄ | H | H | O | 203 |
| 16 | F₃C–(triazolinone-CH₃) | H | H | H | H | 4-Br-C₆H₄ | H | H | O | 241 |
| 17 | H₃C–(triazolinone-CH₃) | H | –CH₂N(CH₃)₂ | H | H | 4-Cl-C₆H₄ | 4Cl | H | O | 229 |
| 18 | Ph–(triazolinone-CH₃) | H | H | H | H | 4-Br-C₆H₄ | 4Cl | H | O | 234 |
| 19 | H₃C–(triazolinone-CH₃) | H | –CH₂N(CH₃)₂ | H | H | 4-Br-C₆H₄ | 4Cl | H | O | 242 |

TABLE 2-continued

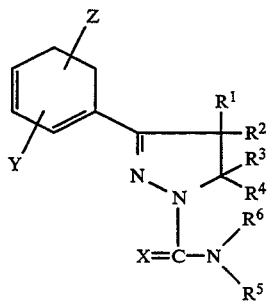

| Example No. | R¹ | R² | R³ | R⁴ | R⁵ | R⁶ | Y | Z | X | Melting point °C. |
|---|---|---|---|---|---|---|---|---|---|---|
| 20 | ![Cl-C6H4-C(=N-N=...)-N(CH3)-C(=O)- triazolinone] | H | H | H | H | ![4-Cl-C6H4-] | 4Cl | H | O | |
| 21 | ![Cl-C6H4-C(=N-N=...)-N(CH3)-C(=O)- triazolinone] | H | H | H | H | ![4-OCF3-C6H4-] | 4Cl | H | O | |
| 22 | ![Cl-C6H4-C(=N-N=...)-N(CH3)-C(=O)- triazolinone] | H | H | H | H | ![4-Br-C6H4-] | 4Cl | H | O | |

PREPARATION OF THE STARTING COMPOUNDS

Example (II-1)

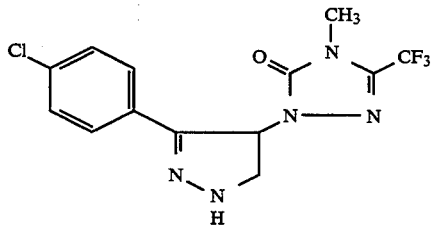

11.2 g (0.035 mol) of α-(4-methyl-3-trifluoromethyl-Δ²-1,2,4-triazolin-5-on-1-yl)-4'-chloroaceto-phenone are dissolved in 100 ml of absolute acetonitrile until a clear solution has formed, 10 g (0.107 mol) of N,N-dimethylmethyleneimmonium chloride are added, and the mixture is refluxed for 4 hours until starting material is no longer visible following TLC checking. 20 ml of hydrazine hydrate are then added at 70° C., and stirring is continued for 10 minutes. The mixture is subsequently concentrated in vacuo, the residue is treated with 200 ml of water, and the mixture is extracted using ethyl acetate. The organic phase is separated, dried over MgSO₄ and concentrated. 12 g (99% of theory) of 3-(4''-chlorophenyl)-4-(4''-methyl-3''-trifluoromethyl-Δ²''-1'',2'',4''-triazolin-5''-on-1''-yl)-4,5-dihydropyrazole are obtained as a pale yellow solid having a melting point of 198° C.

The starting compounds of the formula (II) which are listed below in Table 3 are obtained analogously to Example (II-1) and taking into consideration the information in the description of the processes according to the invention:

TABLE 3

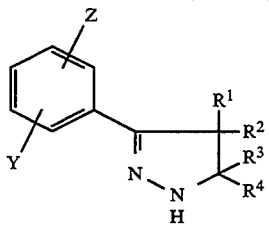
(II)

| Example No. | R¹ | R² | R³ | R⁴ | Y | Z | Physical Constant |
|---|---|---|---|---|---|---|---|
| II-2 | F₃C group with N-CH₃, C=O, N—N— | H | H | H | H | H | ¹H NMR*: (δ=7.3–7.75(5H, m); 6.05(1H, q); 3.71–3.95(2H, m); 3.36(3H, s) |
| II-3 | H₃C group with N-CH₃, C=O, N—N— | H | H | H | 4Cl | H | oil |
| II-4 | H₃C group with N-CH₃, C=O, N—N— | H | CH₂—N(CH₃)₂ | H | 4Cl | H | ¹H NMR**: (δ=5.63(1H, d); 3.95(1H, m); 2.20–2.45(2H, m); 2.2(6H, s)3.1(3H, s); 2.1(3H, s) |
| II-5 | phenyl group with N-CH₃, C=O, N—N— | H | H | H | 4Cl | H | oil |
| II-6 | 4-Cl-phenyl group with N-CH₃, C=O, N—N— | H | H | H | 4Cl | H | oil |

PREPARATION OF THE PRECURSORS

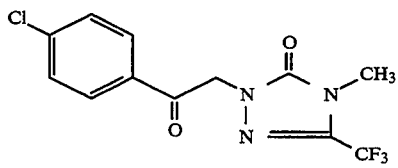
(VIa-1)

1.8 g (0.075 mol) of sodium hydride are suspended in 100 ml of DMF (anhydrous) under a protective gas atmosphere, and 10 g (0.06 mol) of 4-methyl-3-trifluoromethyl-Δ²-1,2,4-triazolin-5-one, dissolved in 100 ml of DMF (anhydrous), are added dropwise to this suspension at 20° C. Stirring is subsequently continued for 3 hours at 60° C. until a clear solution has formed. 14 g (0.06 mole) of 4-chlorophenacyl bromide, dissolved in 100 ml of DMF (anhydrous), are added dropwise to this solution at 20° to 30° C., and stirring is then continued for 1 more hour at room temperature. The reaction mixture is treated with 2 l of water and the solid which precipitates is filtered off with suction and subsequently resuspended in petroleum ether. After filtration with suction, 11.5 g (52% of theory) of α-(4-methyl-3-tri-fluoromethyl-Δ²-1,2,4-triazolin-5-on-1-yl)-4'-chloroacetophenone are obtained as a pale yellow solid.

¹H NMR* (δ=7.48–7.95 (4H,m) 5.37 (2H,s), 3.43 (3H,s).

The precursors of the formula (VIa) which are listed below in Table 4 are obtained analogously to Example (VIa-1) and taking into consideration the information in the description of the processes according to the invention:

TABLE 4

(VIa)

Y—(phenyl with Z)—C(O)—CH₂—R¹

| Example No. | R¹ | Y | Z | Physical Constant |
|---|---|---|---|---|
| (VIa-2) | 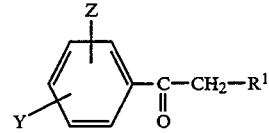 | H | H | oil |

TABLE 4-continued $$\text{(VIa)}$$

Structure: phenyl ring with Z substituent, Y substituent, and C(=O)-CH$_2$-R$^1$ group.

| Example No. | R$^1$ | Y | Z | Physical Constant |
|---|---|---|---|---|
| (VIa-3) | N-methyl-N'-methyl-N'-(1-methylethylidene)hydrazinecarbonyl [C(=O)-N(CH$_3$)-N(CH$_3$)-N=C(CH$_3$)-] | 4Cl | H | 148° C. |
| (VIa-4) | N-methyl-N'-methyl-N'-(phenylmethylidene)hydrazinecarbonyl [C(=O)-N(CH$_3$)-N(CH$_3$)-N=CH-C$_6$H$_5$] | 4Cl | H | 128° C. |
| (VIa-5) | N-methyl-N'-(1-methylthioethylidene)hydrazine-S-carbonyl [C(=O)-S-N(CH$_3$)-N=C(SCH$_3$)-] | 4Cl | H | 126° C. |
| (VIa-6) | N-methyl-N'-(1-methylthioethylidene)hydrazine-S-carbonyl [C(=O)-S-N(CH$_3$)-N=C(SCH$_3$)-] | 4Br | H | 141° C. |
| (VIa-7) | 5-trifluoromethyl-1-methyl-4,5-dihydro-pyrazol-3-yl-carbonyl | 4Cl | H | 112° C. |
| (VIa-8) | N-methyl-N'-(1-trifluoromethylethylidene)hydrazine-O-carbonyl [C(=O)-O-N(CH$_3$)-N=C(CF$_3$)-] | 4Cl | H | oil |
| (VIa-11) | N-methyl-N'-methyl-N'-(4-chlorophenylmethylidene)hydrazinecarbonyl | 4Cl | H | |
| (VIa-9) | N-methyl-N'-methyl-N'-(1-trifluoromethylethylidene)hydrazinethiocarbonyl [C(=S)-N(CH$_3$)-N(CH$_3$)-N=C(CF$_3$)-] | 4Cl | H | |
| (VIa-10) | N-methyl-N'-(1-methylethylidene)pyrazolinonyl | 4Cl | H | |

*The $^1$H NMR spectra were recorded in deuterochloroform (CDCl$_3$) with tetramethylsilane (TMS) as the internal standard. The data given are the chemical shift as δ value in ppm.
**The $^1$H NMR spectra were recorded in deuterated dimethyl sulphoxide (CD$_3$)$_2$SO with tetramethylsilane (TMS) as the internal standard. The data given are the chemical shift as the δ value in ppm.

Use Examples

In the Use Examples which follow, the compounds listed below were employed as comparison substances.

(A) 2-chlorophenyl-CO-NH-CO-NH-phenyl-OCF$_3$

Triflumuron = 2-chloro-N[[[4-(trifluoromethoxy)-phenyl]amino]-carbonyl]-benzamide (disclosed in: DE-A 2,601,780)

(B) (C$_2$H$_5$O)(C$_3$H$_7$S)P(=S)-O-phenyl-SCH$_3$

Sulprofos = O-ethyl O-(4-methylthio)-phenyl S-propyl dithiophosphate (disclosed in: DE-A 2,111,414)

Example A

Phaedon larvae test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of the active compound of the desired concentration and are infested with mustard beetle larvae (Phaedon cochleariae) while the leaves are still moist.

After the specified time, the destruction in % is-determined. 100% means that all the beetle larvae have been killed; 0% means that none of the beetle larvae have been killed.

In this test, a superior activity compared with the prior art is shown, for example, by the following compounds of the Preparation Examples: 1, 5, 6, 7, 8, 10, 11, 12, 13, 14 and 16.

Example B

Heliothis virescens test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soya bean shoots (Glycine max) are treated by being dipped into the preparation of the active compound of the desired concentration and are infested with the tobacco budworm (Heliothis virescens) while the leaves are still moist.

After the specified time, the destruction in % is-determined. 100% means that all the caterpillars have been killed; 0% means that none of the caterpillars have been killed.

In this test, a superior activity compared with the prior art is shown, for example, by the following compounds of the Preparation Examples: 1, 5 and 9.

Example C

Plutella test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of the active compound of the desired concentration and are infested with mustard beetle larvae (Phaedon cochleariae) while the leaves are still moist.

After the specified time, the destruction in % is determined. 100% means that all the beetle larvae have been killed; 0% means that none of the beetle larvae have been killed.

In this test, a superior activity compared with the prior art is shown, for example, by the following compounds of the Preparation Examples: 1, 10 and 11.

Example D

Blowfly larvae test
Test animals: Lucilia cuprina larvae
Emulsifier: 35 parts by weight of ethylene glycol monomethyl ether 35 parts by weight of nonylphenol polyglycol ether To produce a suitable preparation of active compound, three parts by weight of active compound are mixed with seven parts by weight of the abovementioned mixture and the resulting emulsion concentrate is diluted with water to the specific, desired concentration.

Approximately 20 resistant Lucilia cuprina larvae are introduced into a test tube which contains approximately 1 cm$^3$ of horse meat and 0.5 ml of the preparation of active compound. After 24 hours, the activity of the preparation of active compound is determined. 100% means that all blowfly larvae have been killed; 0% means that none of the blowfly larvae have been killed.

In this test, a superior activity compared with the prior art was shown, for example, by the following compounds of the Preparation Examples: 1, 5, 8, 9, 10, 11, 12, 13, 14 and 16.

Example E $LT_{100}$ test
Test animals: Musca domestica, strain WHO-N Solvent:
  35 parts by weight of ethylene glycol monomethyl ether
  35 parts by weight of nonylphenol polyglycol ether To prepare a Suitable formulation, three parts by weight of active compound are mixed with seven parts of the abovementioned solvent/emulsifier mixture, and the resulting emulsion concentrate is diluted with water to the specific, desired concentration.

2 ml of this preparation of active compound are pipetted onto filter paper dishes ($\phi$9.5 cm) which are located in Petrie dishes of a suitable size. After the filter discs have dried, 25 test animals are introduced into the Petrie dish and covered.

The condition of the test animals is monitored continuously for up to 6 hours. The time required for a 100% knock-down effect is determined. If the $LT_{100}$ has not been reached after 6 hours, the percentage of knocked-down test animals is determined.

In this test, an $LT_{100}$ of 100 minutes was shown, for example, by the compound of Preparation Example 8 at an exemplary concentration of 1000 ppm of a.i.

We claim:

1. A substituted carbamoylpyrazoline of the formula

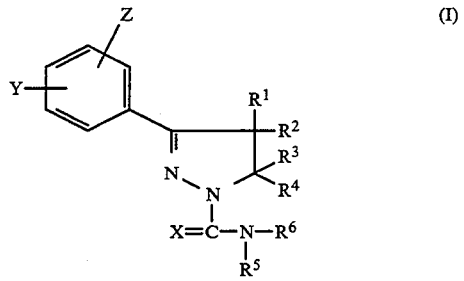

in which $R^1$ represents an azolinone, azolinethione or azolineimino radical, optionally monosubstituted or di-substituted by identical or different substituents and bonded via nitrogen, from the group consisting of

(R$^1$-a)

(R$^1$-b)

(R$^1$-c)

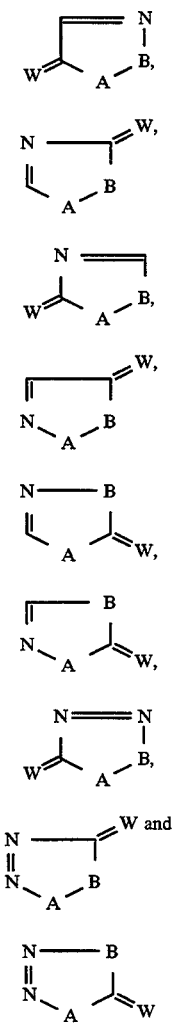

(R¹-d)

(R¹-e)

(R¹-f)

(R¹-g)

(R¹-h)

(R¹-i)

(R¹-k)

(R¹-l)

(R¹-m)

in which
one of the groups A or B represents nitrogen while the other (B or A) represents oxygen, sulphur, the group —N alkyl($C_1$-$C_4$) or a methylene group —$CH_2$—, W represents oxygen, sulphur or the group —N alkyl (—$CH_1$-$C_4$), and the substituents on the azolinone, azolinethione or azolineimino radicals are alkyl ($C_1$-$C_6$), alkoxy ($C_1$-$C_6$), alkyl ($C_1$-$C_6$) thio, amino, alkyl ($C_1$-$C_6$) amino, halogenoalkyl ($C_1$-$C_4$), dialkyl ($C_1$-$C_6$) amino, and phenyl which is optionally substituted by halogen, alkyl ($C_1$-$C_4$), alkoxy ($C_1$-$C_4$), halogenoalkyl ($C_1$-$C_4$), halogenoalkoxy($C_1$-$C_4$)- or halogenoalkyl ($C_1$-$C_4$)thio, $R^2$ represents hydrogen, alkyl ($C_1$-$C_6$), or represents cycloalkyl ($C_3$-$C_7$) which is optionally substituted by halogen or halogenoalkyl-($C_1$-$C_4$); or represents halogenoalkyl ($C_1$-$C_4$), halogenoalkyl ($C_1$-$C_4$) thio or alkoxy ($C_1$-$C_6$)carbonyl, $R^3$ represents hydrogen, alkyl($C_1$-$C_6$) or a group

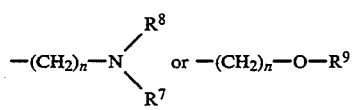

in which
$R^7$ and $R^8$ in each case independently of one another represent hydrogen, alkyl($C_1$-$C_6$), or phenyl which is optionally substituted by alkyl ($C_1$-$C_4$), alkoxy($C_1$-$C_4$), alkyl($C_1$-$C_4$)thio, halogen, halogenoalkyl($C_1$-$C_4$), halogenoalkoxy($C_1$-$C_4$) or halogenoalkyl ($C_1$-$C_4$)thio and $R^9$ represents hydrogen, alkyl($C_1$-$C_6$) or optionally substituted phenyl, wherein the substituents are the same as those recited for $R^8$, and n represents the numbers 1 to 4, $R^4$ represents hydrogen or alkyl ($C_1$-$C_6$), $R^5$ represents hydrogen, alkyl ($C_1$-$C_6$), phenyl or alkyl($C_1$-$C_6$)thio, $R^6$ represents alkyl($C_1$-$C_8$) which is optionally substituted by halogen, halogenoalkyl ($C_1$-$C_4$) or halogenoalkoxy ($C_1$-$C_4$), or represents cycloalkyl ($C_3$-$C_7$) which is optionally substituted by halogen, halogenoalkyl($C_1$-$C_4$) or halogenoalkoxy($C_1$-$C_4$), or represents the radical

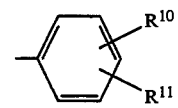

in which
$R^{10}$ and $R^{11}$ can be identical or different and represent halogen, alkyl($C_1$-$C_6$), nitro, cyano, halogenoalkyl($C_1$-$C_4$), alkoxy($C_1$-$C_6$), halogenoalkoxy($C_1$-$C_4$), alkyl($C_1$-$C_4$)thio, halogenoalkyl ($C_1$-$C_4$)thio, or represent phenoxy or phenylthio, each of which is optionally substituted by halogen, halogenoalkyl ($C_1$-$C_4$) or alkoxy($C_1$-$C_4$), or represents mono- or dialkylamino, each of which has 1 to 6 carbon atoms in the alkyl radical and each of which is optionally substituted by halogen, alkoxy($C_1$-$C_4$) or halogenoalkyl($C_1$-$C_4$), or represent cycloalkyl($C_3$-$C_7$) which is optionally substituted by alkyl ($C_1$-$C_4$), alkoxy($C_1$-$C_4$), halogen or alkyl($C_1$-$C_4$)thio, or represent alkoxy($C_1$-$C_4$ )carbonyl, alkenyl(-$C_2$-$C_6$)oxy, alkinyl($C_2$-$C_8$), alkyl($C_1$-$C_4$)thionyl, alkyl($C_1$-$C_4$ ) sulphonyl, halogenoalkyl ($C_1$-$C_4$)thionyl, halogenoalkyl ($C_1$-$C_4$) sulphonyl or halogenoalkoxy ($C_1$-$C_4$ ) carbonyl, or in which $R^{10}$ and $R^{11}$ together represent one of the following bivalent radicals

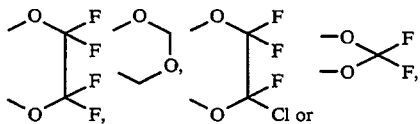

X represents oxygen or sulphur and
Y and Z can be identical or different and represent hydrogen, alkyl ($C_1$-$C_6$), halogen, halogenoalkyl ($C_1$-$C_5$), alkoxy($C_1$-$C_6$), alkyl($C_1$-$C_5$)thio, halogenoalkoxy($C_1$-$C_4$), halogenoalkyl ($C_1$-$C_4$) thio, alkoxy ($C_1$-$C_4$) carbonyl, halogenoalkoxy($C_1$-$C_4$)carbonyl, or represent phenoxy or phenylthio, each of which is optionally substituted by halogen, alkyl($C_1$-$C_4$), alkoxy($C_1$-$C_4$) or halogenoalkyl($C_1$-$C_4$), or represent alkenyl(-$C_1$-$C_6$)oxy, alkinyl ($C_2$-$C_6$), alkyl ($C_1$-$C_4$)thionyl, alkyl ($C_1$-$C_4$)sulphonyl, halogenoalkyl($C_1$-$C_4$)thionyl, halogenoalkyl ($C_1$-$C_4$) sulphonyl, nitro or cyano, or in which Y and Z together represent 3,4-methylenedioxy or 3,4-ethylenedioxy, each of which is optionally substituted by fluorine and/or chlorine.

2. A substituted carbamoylpyrazoline according to claim 1, wherein $R^1$ represents an azolinone, azolinethione or azolineimino radical, optionally monosubstituted or disubstituted by identical or different substituents and bonded via nitrogen, from the group consisting of

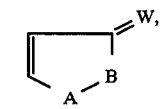 (R$^1$-a)

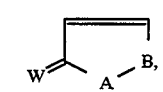 (R$^1$-b)

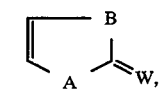 (R$^1$-c)

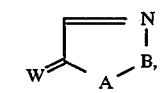 (R$^1$-d)

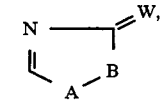 (R$^1$-e)

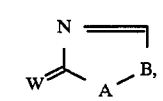 (R$^1$-f)

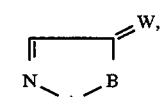 (R$^1$-g)

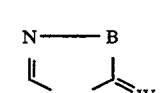 (R$^1$-h)

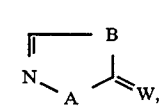 (R$^1$-i)

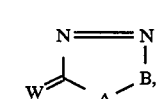 (R$^1$-k)

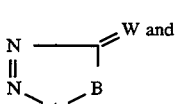 (R$^1$-l)

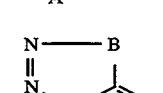 (R$^1$-m)

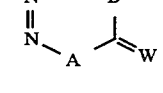

in which one of the groups A or B represents nitrogen and while the other (B or A) represents oxygen, sulphur or the group —N alkyl ($C_1$-$C_4$) or a methylene group —$CH_2$—, W represents oxygen, sulphur or the group —N alkyl($C_1$-$C_4$) and the substituents on the azolinone, azolinethione or azolineino radicals are alkyl ($C_1$-$C_4$), alkoxy ($C_1$-$C_4$), alkyl ($C_1$-$C_4$)thio, amino, alkyl ($C_1$-$C_4$)amino, halogenoalkyl($C_1$-$C_4$), dialkyl ($C_1$-$C_2$) amino and phenyl which is optionally substituted by fluorine, chlorine, bromine, methyl, ethyl, methoxy, ethoxy, halogenoalkyl($C_1$-$C_2$), halogenoalkoxy($C_1$-$C_2$) or halogenoalkyl ($C_1$-$C_2$)thio, $R^2$ represents hydrogen, alkyl ($C_1$-$C_4$), or cycloalkyl ($C_3$-$C_6$) which is optionally substituted by fluorine, chlorine, bromine or halogenoalkyl ($C_1$-$C_3$); or represents halogenoalkyl ($C_1$-$C_3$), halogenoalkyl ($C_1$-$C_3$) thio or alkoxy($C_1$-$C_4$) carbonyl, $R^3$ represents hydrogen, alkyl ($C_1$-$C_4$) or a group

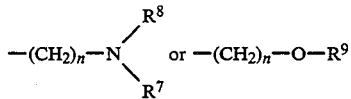

in which $R^7$ and $R^8$ in each case independently of one another represent hydrogen, alkyl($C_1$-$C_4$), or phenyl which is optionally substituted by methyl, ethyl, methoxy, ethoxy, methylthio, ethylthio, fluorine, chlorine, bromine, halogenoalkyl ($C_1$-$C_2$), halogenoalkoxy($C_1$-$C_2$) or halogenoalkyl($C_1$-$C_2$) thio and $R^9$ represents hydrogen alkyl($C_1$-$C_4$), or phenyl, which is optionally monosubstituted or polysubstituted by identical or different substituents, wherein the substituents are the same as those recited for $R^8$ and n represents the numbers 1, 2 or 3, $R^4$ represents hydrogen or alkyl($C_1$-$C_4$), $R^5$ represents hydrogen, alkyl ($C_1$-$C_4$), phenyl or alkyl($C_1$-$C_3$) thio, $R^6$ represents alkyl ($C_1$-$C_4$) which is optionally substituted by fluorine, chlorine, bromine, halogenoalkyl ($C_1$-$C_3$) or halogenoalkoxy ($C_1$-$C_3$), or represents cycloalkyl($C_3$-$C_6$) which is optionally substituted by fluorine, chlorine, bromine, halogenoalkyl($C_1$-$C_3$) or halogenoalkoxy($C_1$-$C_3$), or represents the radical

which $R^{10}$ and $R^{11}$ can be identical or different and represent fluorine, chlorine, bromine, iodine, alkyl ($C_1$-$C_4$), nitro, cyano, halogenoalkyl ($C_1$-$C_3$), alkoxy($C_1$-$C_4$), halogenoalkoxy ($C_1$-$C_3$), alkyl($C_1$-$C_3$) thio or halogenoalkyl ($C_1$-$C_3$)thio, or represent phenoxy which is optionally substituted by fluorine, chlorine, bromine, halogenoalkyl ($C_1$-$C_3$) or alkoxy($C_1$-$C_4$), or represent mono- or dialkylamino, each of which has 1 to 4 carbon atoms in the alkyl radical and each of which is optionally substituted by fluorine, chlorine, bromine, alkoxy($C_1$-$C_3$) or halogenoalkyl($C_1$-$C_3$), or represent cycloalkyl($C_3$-$C_6$) which is optionally substituted by alkyl($C_1$-$C_3$), alkoxy($C_1$-$C_3$), fluorine, chlorine, bromine or alkyl ($C_1$-$C_3$) thio, or in which $R^{10}$ and $R^{11}$ together represent one of the following bivalent radicals

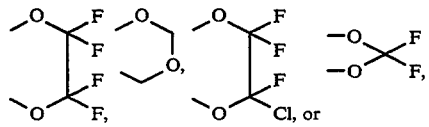

X represents oxygen or sulphur and

Y and Z can be identical or different and represent hydrogen, alkyl($C_1$-$C_4$), fluorine, chlorine, bromine, halogenoalkyl($C_1$-$C_4$), alkoxy($C_1$-$C_4$), alkyl ($C_1$-$C_4$) thio, halogenoalkoxy ($C_1$-$C_3$), halogenoalkyl ($C_1$-$C_3$)thio, alkoxy($C_1$-$C_3$)carbonyl, or phenoxy or phenylthio, each of which is optionally substituted by fluorine, chlorine, bromine, alkyl ($C_1$-$C_3$), alkoxy ($C_1$-$C_3$) or halogenoalkyl($C_1$-$C_3$), or represent alkenyl ($C_2$-$C_4$)oxy, alkinyl($C_2$-$C_4$), alkyl($C_1$-$C_3$)thionyl, alkyl($C_1$-$C_4$)sulphonyl, halogenoalkyl($C_1$-$C_3$)thionyl, halogenoalkyl ($C_1$-$C_3$)sulphonyl, nitro or cyano, or in which Y and Z together represent 3,4-methylenedioxy or 3,4-ethylenedioxy, each of which is optionally substituted by fluorine and/or chlorine.

3. A substituted carbamoylpyrazoline according to claim 1, wherein $R^1$ represents an azolinone, azolinethione or azolineimino radical, in each case optionally monosubstituted or disubstituted by identical or different substituents and bonded via nitrogen, from the group consisting of

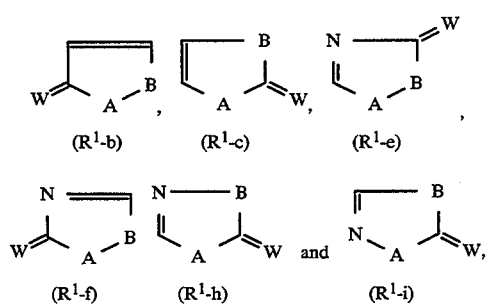

in which
one of the groups A or B represents nitrogen while other (B or A) represents oxygen, sulphur, —NCH₃ or a methylene group —CH₂—, W represents oxygen or sulphur, and the substituents on the azolinone, azolinethione or azolineimino radicals are methyl, ethyl, n-propyl, i-propyl, t-butyl, methoxy, methylthio, trifluoromethyl, chlorodifluoromethyl, fluorodichloromethyl, and phenyl which is optionally substituted by fluorine, chlorine, bromine, methyl, methoxy, trifluoromethyl or trifluoromethoxy $R^2$ represents hydrogen, methyl, ethyl, n-propyl, i-propyl or alkoxy($C_1$-$C_2$)carbonyl, $R^3$ represents hydrogen, methyl, ethyl, n-propyl, i-propyl or the group

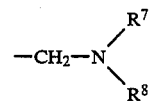

in which $R^7$ and $R^8$ in each case independently of one another represent hydrogen, methyl, ethyl, n-propyl or i-propyl, $R^4$ represents hydrogen, methyl, ethyl or n-propyl, $R^5$ represents hydrogen, methyl, ethyl, n-propyl, i-propyl, phenyl or alkyl($C_1$-$C_2$)thio, $R^6$ represents methyl, ethyl, n-propyl or i-propyl, each of which is optionally substituted by fluorine, chlorine, halogenoalkyl($C_1$-$C_3$) or halogenoalkoxy($C_1$-$C_3$), or represents cycloalkyl($C_3$-$C_6$) which is optionally substituted by fluorine, halogenoalkyl ($C_1$-$C_3$) or halogenochlorine, alkoxy ($C_1$-$C_3$), or represents the radical

in which $R^{10}$ and $R^{11}$ can be identical or different and represent fluorine, chlorine, bromine, iodine, methyl, ethyl, n-propyl, i-propyl, tert.-butyl, nitro, cyano, halogenoalkyl($C_1$-$C_3$), alkoxy($C_1$-$C_3$), halogenoalkoxy ($C_1$-$C_3$), alkyl($C_1$-$C_3$)thio, halogenoalkyl ($C_1$-$C_3$) thio, or represent phenoxy which is optionally substituted by fluorine, chlorine, halogenoalkyl($C_1$-$C_3$), methoxy, ethoxy, methyl or ethyl, or represent mono- or dialkylamino, each of which has 1 to 3 carbon atoms in the alkyl radical and each of which is optionally substituted by fluorine, chlorine, methoxy, ethoxy or halogenoalkyl ($C_1$-$C_3$), or represent cycloalkyl ($C_3$-$C_6$) which is optionally substituted by methyl, ethyl, methoxy, ethoxy, fluorine, chlorine or alkyl ($C_1$-$C_3$) thio, or in which $R^{10}$ and $R^{11}$ together represent one of the following bivalent radicals

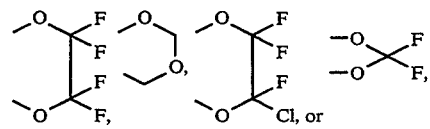

X represents oxygen or sulphur and

Y and Z can be identical or different and represent hydrogen, methyl, ethyl, n-propyl, i-propyl, fluorine, chlorine, halogenoalkyl ($C_1$-$C_3$), methoxy, ethoxy, n-propyloxy, i-propyloxy, alkyl($C_1$-$C_3$)thio, halogenoalkoxy($C_1$-$C_3$), halogenoalkyl($C_1$-$C_3$)thio, alkoxy($C_1$-$C_3$)carbonyl, or represent phenoxy or phenylthio, each of which is optionally substituted by fluorine, chlorine, methyl, ethyl, methoxy, ethoxy or halogenoalkyl ($C_1$-$C_3$), or represent alkenyl($C_3$-$C_4$)oxy, alkinyl($C_2$-$C_4$), alkyl($C_1$-$C_3$)thionyl, alkyl($C_1$-$C_3$)sulphonyl, halogenoalkyl ($C_1$-$C_3$)thionyl, halogenoalkyl ($C_1$-$C_3$)sulphonyl, nitro or cyano, or in which Y and Z together represent 3,4-methylenedioxy or 3,4-ethylenedioxy, each of which is optionally substituted by fluorine and/or chlorine.

4. A pesticidal composition comprising a pesticidally effective amount of a substituted carbamoylpyrazoline according to claim 1, and an inert diluent or carrier.

5. A method of combating pests which comprises contacting the pests and/or their environment with a pesticidally effective amount of a substituted carbamoylpyrazoline according to claim 1.

* * * * *

UNITED STATES PATENT AND TRADEMARK OFFICE
CERTIFICATE OF CORRECTION

PATENT NO. : 5,391,560
DATED : February 21, 1995
INVENTOR(S) : Fuchs, et al.

It is certified that error appears in the above-indentified patent and that said Letters Patent is hereby corrected as shown below:

| | |
|---|---|
| Col. 106, line 15 | Delete " $(C_1-C_8)$ " and substitute -- $(C_1-C_6)$ -- |
| Col. 106, line 44 | Delete " $(C_2-C_8)$ " and substitute -- $(C_2-C_6)$ -- |
| Col. 106, line 61 | Delete " $(C_1-C_5)$ " and substitute -- $(C_1-C_6)$ --, delete " alkyl$(C_1-C_5)$ thio " and substitute -- alkyl$(C_1-C_6)$ thio -- |
| Col. 106, last line | Delete " $C_1-C_6$)oxy " and substitute -- $C_2-C_6$)oxy -- |
| Col. 108, line 8 | Delete " $(C_1-C_2)$ " and substitute -- $(C_1-C_4)$ -- |
| Col. 110, line 21 | After " fluorine, " insert -- chlorine -- |

UNITED STATES PATENT AND TRADEMARK OFFICE
CERTIFICATE OF CORRECTION

PATENT NO. : 5,391,560
DATED : February 21, 1995
INVENTOR(S) : Fuchs, et al.

It is certified that error appears in the above-indentified patent and that said Letters Patent is hereby corrected as shown below:

Col. 110, line 22   Delete " halogenochlorine, alkoxy " and substitute -- halogenoalkoxy --

Signed and Sealed this

Ninth Day of May, 1995

Attest:

BRUCE LEHMAN

*Attesting Officer*              *Commissioner of Patents and Trademarks*